United States Patent
Akin et al.

(10) Patent No.: US 6,287,286 B1
(45) Date of Patent: *Sep. 11, 2001

(54) **ABSORBENT ARTICLE HAVING A REDUCED VIABILITY OF *CANDIDA ALBICANS***

(75) Inventors: Frank Jerrel Akin, Marietta; Pamela Jean Mayberry, Roswell; Susan Carol Paul, Alpharetta; Audra Stefanik Wright, Woodstock, all of GA (US); Michael John Faulks, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/328,681

(22) Filed: Jun. 9, 1999

Related U.S. Application Data
(60) Provisional application No. 60/097,810, filed on Aug. 25, 1998.

(51) Int. Cl.[7] .................................................. A61F 13/15
(52) U.S. Cl. .............................. 604/385.01; 604/385.23
(58) Field of Search ............................. 604/385.01, 359, 604/360

(56) References Cited

U.S. PATENT DOCUMENTS

| | | |
|---|---|---|
| 3,371,667 | 3/1968 | Morse . |
| 3,431,911 | 3/1969 | Meisel, Jr. . |
| 3,563,243 | 2/1971 | Lindquist . |
| 3,805,790 | 4/1974 | Kaczmarzyk et al. . |
| 3,916,900 | 11/1975 | Breyer et al. . |
| 3,945,386 | 3/1976 | Anczurowski et al. . |
| 4,055,184 | 10/1977 | Karami . |
| 4,100,324 | 7/1978 | Anderson et al. . |
| 4,233,212 | 11/1980 | Otoi et al. . |
| 4,276,338 | 6/1981 | Ludwa et al. . |
| 4,306,559 | 12/1981 | Nishizawa et al. . |

(List continued on next page.)

FOREIGN PATENT DOCUMENTS

| | | |
|---|---|---|
| 0 343 941 A2 | 11/1989 | (EP) . |
| 0 774 242 A1 | 5/1997 | (EP) . |
| 0 797 968 A1 | 10/1997 | (EP) . |

(List continued on next page.)

OTHER PUBLICATIONS

American Society for Testing Materials (ASTM) Designation: D 1321–92, "Standard Test Method for Needle Penetration of Petroleum Waxes," pp. 483–485, published Dec. 1992.

American Society for Testing Materials (ASTM) Designation: D 3236–88, "Standard Test Method for Apparent Viscosity of Hot Melt Adhesives and Coating Materials," pp. 326–331, published Dec. 1988.

Anderson, P.H. et al., "Faecal Enzymes: In Vivo Human Skin Irritation," *Contact Dermatitis*, vol. 30, No. 3, 1994, pp. 152–158.

(List continued on next page.)

*Primary Examiner*—Dennis Ruhl
(74) *Attorney, Agent, or Firm*—Jeffrey B. Curtin

(57) ABSTRACT

An absorbent article includes a vapor permeable backsheet, a liquid permeable topsheet positioned in facing relation with the backsheet; and an absorbent body located between the backsheet and the topsheet which defines multiple zones of high air permeability. The absorbent article may also include a ventilation layer between the absorbent body and the backsheet and a surge management layer between the absorbent body and the topsheet. The article exhibits improved air exchange within the article during use. As a result, the article exhibits substantially reduced levels of hydration of the wearer's skin when in use which renders the skin less susceptible to the viability of microorganisms.

25 Claims, 4 Drawing Sheets

U.S. PATENT DOCUMENTS

| | | |
|---|---|---|
| 4,389,211 | 6/1983 | Lenaghan . |
| 4,542,199 | 9/1985 | Kaminsky et al. . |
| 4,560,372 | 12/1985 | Pieniak . |
| 4,568,341 | 2/1986 | Mitchell et al. . |
| 4,592,751 | 6/1986 | Gegelys . |
| 4,604,313 | 8/1986 | McFarland et al. . |
| 4,608,292 | 8/1986 | Lassen . |
| 4,624,666 | 11/1986 | DeRossett et al. . |
| 4,634,440 | 1/1987 | Widlund et al. . |
| 4,676,786 | 6/1987 | Nishino . |
| 4,704,112 | 11/1987 | Suzuki et al. . |
| 4,731,065 | 3/1988 | Yamada . |
| 4,781,710 | 11/1988 | Megison et al. . |
| 4,787,896 | 11/1988 | Houghton et al. . |
| 4,798,603 | 1/1989 | Meyer et al. . |
| 4,809,493 | 3/1989 | Genba et al. . |
| 4,839,165 | 6/1989 | Hoppe et al. . |
| 4,839,168 | 6/1989 | Abe et al. . |
| 4,840,692 | 6/1989 | Kamstrup-Larsen . |
| 4,906,460 | 3/1990 | Kim et al. . |
| 4,908,026 | 3/1990 | Sukiennik et al. . |
| 4,990,147 | 2/1991 | Freeland . |
| 5,009,813 | 4/1991 | Watanabe et al. . |
| 5,030,229 | 7/1991 | Yang . |
| 5,061,260 | 10/1991 | Callahan et al. . |
| 5,062,840 | 11/1991 | Holt et al. . |
| 5,064,802 | 11/1991 | Stevens et al. . |
| 5,069,898 | 12/1991 | Goldberg . |
| 5,078,710 | 1/1992 | Suda et al. . |
| 5,137,525 | 8/1992 | Glassman . |
| 5,141,794 | 8/1992 | Arroyo . |
| 5,171,236 | 12/1992 | Dreier et al. . |
| 5,171,238 | 12/1992 | Kajander . |
| 5,176,668 | 1/1993 | Bernardin . |
| 5,176,672 | 1/1993 | Bruemmer et al. . |
| 5,189,192 | 2/1993 | LaPointe et al. . |
| 5,192,277 | 3/1993 | Chung et al. . |
| 5,192,606 | 3/1993 | Proxmire et al. . |
| 5,204,429 | 4/1993 | Kaminsky et al. . |
| 5,263,948 | 11/1993 | Karami et al. . |
| 5,272,236 | 12/1993 | Lai et al. . |
| 5,278,272 | 1/1994 | Lai et al. . |
| 5,294,478 | 3/1994 | Wanek et al. . |
| 5,300,053 | 4/1994 | Genaro . |
| 5,304,161 | 4/1994 | Noel et al. . |
| 5,306,266 | 4/1994 | Freeland . |
| 5,324,278 | 6/1994 | Visscher et al. . |
| 5,349,100 | 9/1994 | Mintz . |
| 5,350,624 | 9/1994 | Georger et al. . |
| 5,352,749 | 10/1994 | DeChellis et al. . |
| 5,356,405 | 10/1994 | Thompson et al. . |
| 5,364,382 | 11/1994 | Latimer et al. . |
| 5,366,451 | 11/1994 | Levesque . |
| 5,366,452 | 11/1994 | Widlund et al. . |
| 5,374,696 | 12/1994 | Rosen et al. . |
| 5,383,870 | 1/1995 | Takai et al. . |
| 5,387,209 | 2/1995 | Yamamoto et al. . |
| 5,391,160 | 2/1995 | Runeman et al. . |
| 5,397,316 | 3/1995 | LaVon et al. . |
| 5,439,458 | 8/1995 | Noel et al. . |
| 5,451,442 | 9/1995 | Pieniak et al. . |
| 5,462,541 | 10/1995 | Bruemmer et al. . |
| 5,482,765 | 1/1996 | Bradley et al. . |
| 5,486,166 | 1/1996 | Bishop et al. . |
| 5,490,846 | 2/1996 | Ellis et al. . |
| 5,505,720 | 4/1996 | Walters et al. . |
| 5,509,915 | 4/1996 | Hanson et al. . |
| 5,514,104 | 5/1996 | Cole et al. . |
| 5,514,105 | 5/1996 | Goodman, Jr. et al. . |
| 5,514,120 | 5/1996 | Johnston et al. . |
| 5,520,674 | 5/1996 | Lavon et al. . |
| 5,533,991 | 7/1996 | Kirby et al. . |
| 5,536,264 | 7/1996 | Hsueh et al. . |
| 5,549,775 | 8/1996 | Odorzynski . |
| 5,558,655 | 9/1996 | Jezzi et al. . |
| 5,558,658 | 9/1996 | Menard et al. . |
| 5,562,650 | 10/1996 | Everett et al. . |
| 5,569,226 | 10/1996 | Cohen et al. . |
| 5,571,096 | 11/1996 | Dobrin et al. . |
| 5,591,148 | 1/1997 | McFall et al. . |
| 5,593,399 | 1/1997 | Tanzer et al. . |
| 5,603,707 | 2/1997 | Trombetta et al. . |
| 5,609,587 | 3/1997 | Roe . |
| 5,611,790 | 3/1997 | Osborn, III et al. . |
| 5,613,962 | 3/1997 | Kenmochi et al. . |
| 5,614,283 | 3/1997 | Potnis et al. . |
| 5,624,422 | 4/1997 | Allen . |
| 5,628,737 | 5/1997 | Dorbin et al. . |
| 5,637,105 | 6/1997 | Tanaka et al. . |
| 5,641,441 | 6/1997 | Yang . |
| 5,643,238 | 7/1997 | Baker . |
| 5,643,239 | 7/1997 | Bodford et al. . |
| 5,643,240 | 7/1997 | Jackson et al. . |
| 5,653,702 | 8/1997 | Brohammer et al. . |
| 5,662,633 | 9/1997 | Doak et al. . |
| 5,662,634 | 9/1997 | Yamamoto et al. . |
| 5,669,895 | 9/1997 | Murakami et al. . |
| 5,669,896 | 9/1997 | Kielpikowski . |
| 5,674,212 | 10/1997 | Osborn, III et al. . |
| 5,674,214 | 10/1997 | Visscher et al. . |
| 5,677,028 | 10/1997 | Ravella . |
| 5,683,375 | 11/1997 | Osborn, III et al. . |
| 5,695,487 | 12/1997 | Cohen et al. . |
| 5,702,382 | 12/1997 | Osborn, III et al. . |
| 6,152,906 * | 11/2000 | Faulks et al. .................. 604/385.01 |

FOREIGN PATENT DOCUMENTS

| | | |
|---|---|---|
| 0 804 914 A1 | 11/1997 | (EP) . |
| 0 813 848 A1 | 12/1997 | (EP) . |
| 0 875 233 A1 | 11/1998 | (EP) . |
| 2 296 438 A | 7/1996 | (GB) . |
| WO 91/00719 A1 | 1/1991 | (WO) . |
| WO 92/11830 A2 | 7/1992 | (WO) . |
| WO 95/05139 A1 | 2/1995 | (WO) . |
| WO 95/13042 A1 | 5/1995 | (WO) . |
| WO 95/17869 A1 | 7/1995 | (WO) . |
| WO 95/17870 A1 | 7/1995 | (WO) . |
| WO 96/00545 A1 | 1/1996 | (WO) . |
| WO 96/03947 A1 | 2/1996 | (WO) . |
| WO 96/12457 A1 | 5/1996 | (WO) . |
| WO 96/15748 A3 | 5/1996 | (WO) . |
| WO 96/20670 A1 | 7/1996 | (WO) . |
| WO 96/20671 A1 | 7/1996 | (WO) . |
| WO 96/21409 A3 | 7/1996 | (WO) . |
| WO 96/34589A2 | 11/1996 | (WO) . |
| WO 97/11660 A1 | 4/1997 | (WO) . |

| | | |
|---|---|---|
| WO 97/14385 A1 | 4/1997 | (WO). |
| WO 97/17923 A1 | 5/1997 | (WO). |
| WO 97/24097 A1 | 7/1997 | (WO). |
| WO 97/34557 A1 | 9/1997 | (WO). |
| WO 97/34558 A1 | 9/1997 | (WO). |
| WO 97/34559 A1 | 9/1997 | (WO). |
| WO 97/36562 A1 | 10/1997 | (WO). |
| WO 98/19861 A2 | 5/1998 | (WO). |
| WO 98/58607 A1 | 12/1998 | (WO). |
| WO 98/58608 A1 | 12/1998 | (WO). |
| WO 98/58609 A1 | 12/1998 | (WO). |
| WO 98/58610 A1 | 12/1998 | (WO). |
| WO 98/58611 A1 | 12/1998 | (WO). |
| WO 98/58615 A1 | 12/1998 | (WO). |

OTHER PUBLICATIONS

Coates, Geoffrey W. and Robert M. Waymouth, "Oscillating Stereocontrol: A Strategy for the Synthesis of Thermoplastic Elastomeric Polypropylene," *Science*, vol. 267, Jan. 13, 1995, pp. 217–219.

"Molecular Weight Distributions," *Encyclopedia of Polymer Science and Engineering*, vol. 3, John Wiley & Sons, New York, 1985, pp. 299–300.

Wagener, K.B., "Oscillating Catalysts: A New Twist for Plastics," *Science*, vol. 267, Jan. 13, 1995, p. 191.

Berglund, Larry G. and Frank J. Akin, "Measurement Of Air Exchange In Diapers By Tracer Gas Methods," *Tappi Journal*, vol. 80, No. 9, Sep. 1997, pp. 173–178.

Federal Test Method Standard (FTMS) No. 191 A, Method 5450, "Permeability To Air; Cloth; Calibrated Orifice Method," Jul. 20, 1978, 5 pages.

Federal Test Method Standard (FTMS) No. 191A, Method 5514, "Water Resistance of Cloth; Low Range, Hydrostatic Pressure Method," Jul. 20, 1978, 3 pages.

Williamson, P. and A.M. Kligman, "A New Method For Quantitative Investigation of Cutaneous Bacteria," *Journal of Investigative Dermatology*, 45:498–503, 1965.

* cited by examiner

ABSORBENT ARTICLE HAVING A REDUCED VIABILITY OF CANDIDA ALBICANS

This application claims priority under 35 U.S.C. § 119(e) from presently copending U.S. provisional application serial No. 60/097,810 entitled "Absorbent Article Having a Reduced Growth of *Candida Albicans*" and filed on Aug. 25, 1998 in the name of Frank J. Akin, Pamela J. Mayberry, Susan C. Paul, Audra S. Wright and Michael J. Faulks.

BACKGROUND OF THE INVENTION

1. Field of the Invention

The present invention relates to an absorbent article for absorbing body fluids and exudates, such as urine. More particularly, the present invention relates to absorbent garments, such as disposable diapers and adult incontinence garments, which are configured to absorb body exudates while also helping to provide reduced skin hydration.

2. Description of the Related Art

Many known diaper configurations employ absorbent materials located between a liquid pervious topsheet and a vapor and liquid impermeable backsheet. Such backsheets are well suited to prevent the migration of liquid waste from the absorbent materials to the outer garments of a wearer. Unfortunately, the use of liquid and vapor impermeable backsheets can result in a high degree of humidity within the diaper when in use which may result in relatively high skin hydration levels. The occlusive, moist environment inside diapers incorporating such backsheets can promote the viability of microorganisms, including *Candida albicans*, which can undesirably lead to the onset of diaper dermatitis (diaper rash).

Diaper dermatitis can afflict almost every infant at some time during the diaper wearing years. The most severe form of this condition is usually caused by secondary infection with the fungi *Candida albicans*. Although other factors influence the pathogenesis of this fungi, one critical factor is the relative humidity within the diaper which is directly related to the occlusion or semi-occlusion of the diaper area.

In order to reduce the humidity level within diapers, breathable polymer films have been employed as outer covers for absorbent garments, such as disposable diapers. The breathable films are typically constructed with micropores to provide desired levels of liquid impermeability and air permeability. Other disposable diaper designs have been arranged to provide breathable regions in the form of breathable panels or perforated regions in otherwise vapor-impermeable backsheets to help ventilate the garment.

Conventional absorbent articles, such as those described above, have not been completely satisfactory. For example, articles which employ perforated films or breathable panels can exhibit excessive leakage of liquids from the article and can excessively soil the wearer's outer garments in the regions of the perforations or panels. In addition, when the absorbent material of the article becomes loaded with liquid, the wet absorbent can block the escape of moisture from the wearer's skin. Such absorbent garment designs have not been able to maintain a high level of breathability when wet to sufficiently reduce the hydration of the wearer's skin. As a result, the wearer's skin has remained susceptible to rashes, abrasion and irritation.

SUMMARY OF THE INVENTION

In response to the difficulties and problems discussed above, a new disposable absorbent article which has a high air exchange rate when wet, reduced levels of skin hydration and a reduced viability of microorganisms has been discovered.

As used herein, reference to "air exchange" refers to the transfer of air from the interior of a diaper, when in use on a wearer, to the exterior of the diaper (ambient atmosphere).

As used herein, a substantially liquid impermeable material is constructed to provide a hydrohead of at least about 60 cm (centimeters), desirably at least about 80 cm, and more desirably at least about 100 cm. A suitable technique for determining the hydrohead value is the Hydrostatic Pressure Test which is described in further detail herein below.

As used herein, a substantially vapor permeable material is constructed to provide a water vapor transmission rate (WVTR) of at least about 100 g/sq.m/24 hr, desirably at least about 250 g/sq.m/24 hr, and more desirably at least about 500 g/sq.m/24 hr. A suitable technique for determining the WVTR value is the Water Vapor Transmission Rate Test which is described in further detail herein below.

In one aspect, the present invention relates to an absorbent article which comprises an absorbent, a front waist section, a rear waist section and an intermediate section which interconnects the front and rear waist sections. The absorbent article defines a Wet Air Exchange Rate of at least about 190 cubic centimeters per minute calculated according to the Tracer Gas Test set forth herein. In a particular embodiment, the article defines a Wet Air Exchange Rate of at least about 200, desirably at least about 225 and more desirably at least about 250 cubic centimeters per minute calculated according to the Tracer Gas Test. The absorbent article may further define a Dry Air Exchange Rate of at least about 525 cubic centimeters per minute calculated according to the Tracer Gas Test and/or a Skin Hydration Value of less than about 18 grams per square meter per hour calculated according to a Skin Hydration Test set forth herein.

In another aspect, the present invention relates to a disposable absorbent article which comprises an absorbent, a front waist section, a rear waist section and an intermediate section which interconnects the front and rear waist sections. The absorbent article defines a Skin Hydration Value of less than about 18 grams per square meter per hour calculated according to the Skin Hydration Test set forth herein. In a particular embodiment, the absorbent article may define a Skin Hydration Value of less than about 15, desirably less than about 12 and more desirably less than about 10 grams per square meter per hour calculated according to the Skin Hydration Test. The absorbent article may further define a Wet Air Exchange Rate of at least about 190 cubic centimeters per minute and/or a Dry Air Exchange Rate of at least about 525 cubic centimeters per minute calculated according to the Tracer Gas Test as set forth herein.

In another aspect, the present invention relates to a disposable absorbent article which defines a front waist section, a rear waist section, and an intermediate section which interconnects the front and rear waist sections. The absorbent article includes a) a vapor permeable backsheet which defines a Water Vapor Transmission Rate of at least about 1000 grams per square meter per 24 hours calculated according to a Water Vapor Transmission Test as set forth herein; b) a liquid permeable topsheet which is positioned in facing relation with the backsheet; and c) an absorbent body located between the backsheet and the topsheet which defines multiple zones of high air permeability for improved air exchange. In a particular embodiment, the zones of high air permeability in the absorbent body define a Frazier Porosity which is at least about 10 percent greater than a Frazier Porosity of portions of the absorbent body adjacent to the zones of high air permeability. The absorbent article may further include a ventilation layer located between the backsheet and the absorbent body.

In still another aspect, the present invention relates to a disposable absorbent article which defines a front waist section, a rear waist section, and an intermediate section which interconnects the front and rear waist sections. The absorbent article includes a) a vapor permeable, liquid impermeable backsheet which defines a Water Vapor Transmission Rate of at least about 1000 grams per square meter per 24 hours calculated according to a Water Vapor Transmission Test as set forth herein; b) a liquid permeable topsheet which is positioned in facing relation with the backsheet; c) an absorbent body located between the backsheet and the topsheet; d) a ventilation layer located between the backsheet and the absorbent body; and e) a surge management layer located between the topsheet and the absorbent body. In a particular embodiment, the absorbent body of the absorbent article includes a plurality of zones of high air permeability for improved air exchange which define a Frazier Porosity which is at least about 10 percent greater than a Frazier Porosity of portions of the absorbent body adjacent to the zones.

In yet another aspect, the present invention relates to a disposable absorbent article which includes an absorbent, a front waist section, a rear waist section and an intermediate section which interconnects the front and rear waist sections. The absorbent article defines a *C. albicans* viability which is less than about 85 percent of the *C. albicans* viability of a control calculated according to a *C. albicans* Viability Test as set forth herein. In a particular embodiment, the *C. albicans* viability is less than about 80 percent and desirably less than about 60 percent of the *C. albicans* viability of the control calculated according to the *C. albicans* Viability Test. The absorbent article may further define a Wet Air Exchange Rate of at least about 190 cubic centimeters per minute and/or a Dry Air Exchange Rate of at least about 525 cubic centimeters per minute calculated according to the Tracer Gas Test as set forth herein and/or a Skin Hydration Value of less than about 18 grams per square meter per hour calculated according to the Skin Hydration Test set forth herein.

The present invention advantageously provides improved absorbent articles which exhibit substantially reduced levels of hydration of the wearer's skin when in use compared to conventional absorbent articles. The reduced level of skin hydration promotes drier, more comfortable skin and renders the skin less susceptible to the viability of microorganisms. Thus, wearer's of absorbent articles made according to the present invention have reduced skin hydration which can lead to a reduction in the incidence of skin irritation and rash.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

Figure 1:
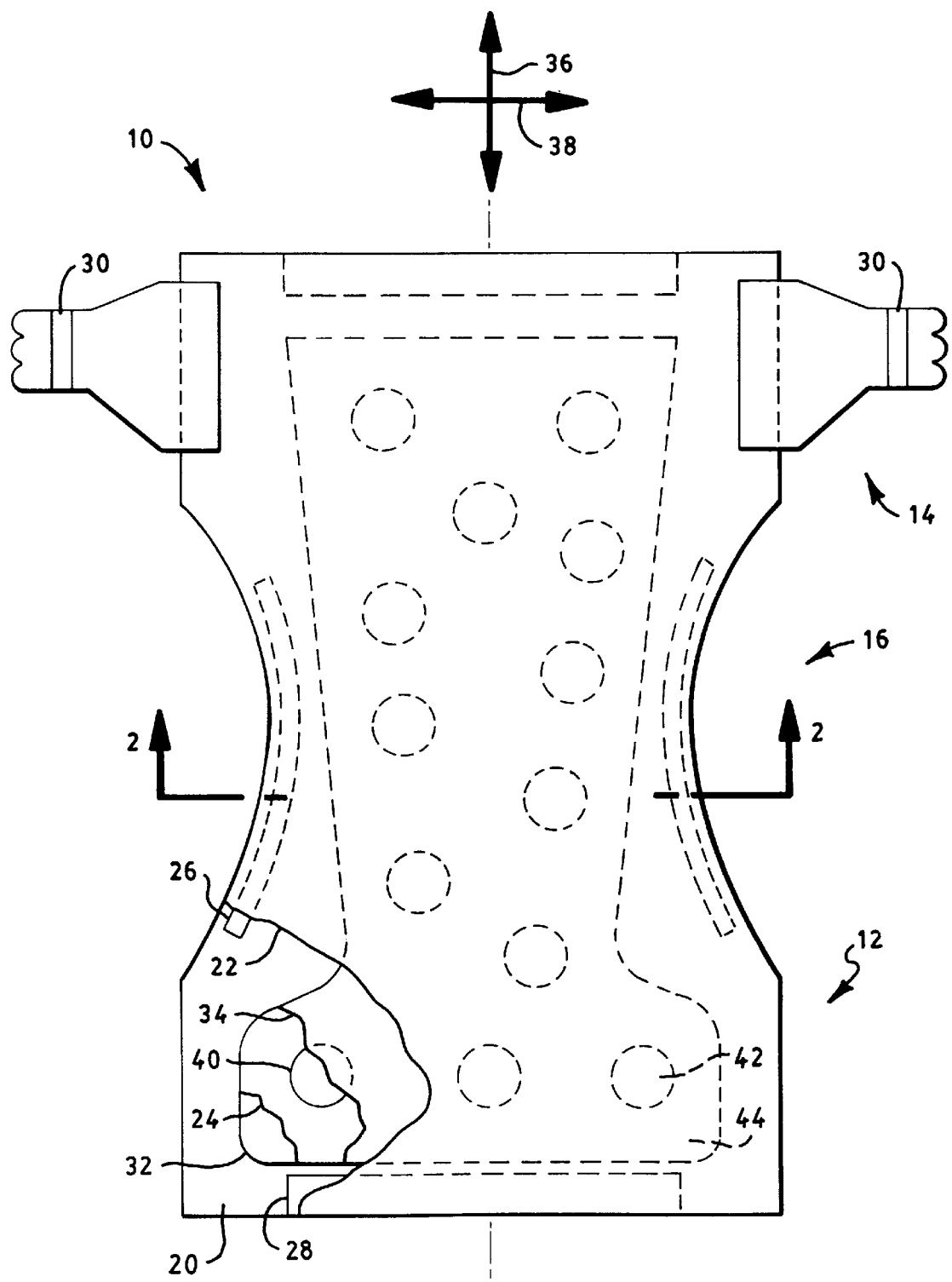
FIG. 1 representatively shows a partially cutaway, top plan view of an absorbent article according to one embodiment of the invention.

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like.

The absorbent articles of present invention advantageously exhibit a substantially reduced level of hydration of the wearers skin in use when compared to conventional absorbent articles. Thus, wearers of absorbent articles of the different aspects of the present invention have reduced skin hydration which renders the skin less susceptible to the viability of microorganisms which can lead to a reduction in the incidence of skin irritation and rash. It has been discovered that the ability of the absorbent articles of the present invention to exhibit a low level of hydration on the wearer's skin during use depends, at least in part, on the ability of the absorbent article to achieve a high rate of air exchange within the article. Moreover, it has been further discovered that the achievement of such low levels of skin hydration further depends on the ability of the article to maintain the high rate of air exchange even when wet.

The ability of an absorbent article to achieve high rates of air exchange both when dry and when wet has, for the purposes of this application, been quantified as the Dry Air Exchange Rate, the Wet Air Exchange Rate and the Wet Air Exchange Rate/Dry Air Exchange Rate ratio as determined according to the Tracer Gas Test set forth below. Briefly, the Tracer Gas Test involves injecting a tracer gas at a constant rate inside the absorbent article next to the skin of the wearer while the article is being worn. Simultaneously, the concentration of the tracer gas in the air space between the article and the wearer is measured by withdrawing a sample at the same constant rate as the injection. The air exchange is then determined based on mass balances of the tracer gas and the air within the space in question.

To achieve the desired low levels of skin hydration, the absorbent articles of the different aspects of the present invention may be constructed to define a Wet Air Exchange Rate of at least about 190 cubic centimeters per minute, generally at least about 200 cubic centimeters per minute, desirably at least about 225 cubic centimeters per minute, more desirably at least about 250 cubic centimeters per minute, and even more desirably at least about 300 cubic centimeters per minute. For example, the absorbent articles may define a Wet Air Exchange Rate of from about 175 to about 1500 cubic centimeters per minute and desirably from about 225 to about 1500 cubic centimeters per minute. Absorbent articles which exhibit Wet Air Exchange Rates less than those above do not allow a sufficient amount of air exchange and undesirably result in increased levels of skin hydration. Such increased levels of skin hydration can render the skin more susceptible to the viability of microorganisms which can undesirably lead to an increase in the incidence of skin irritation and rash.

The absorbent articles of the different aspects of the present invention may further be constructed to define a Dry Air Exchange Rate of at least about 525 cubic centimeters per minute, generally at least about 575 cubic centimeters per minute, desirably at least about 625 cubic centimeters per minute, more desirably at least about 675 cubic centimeters per minute, and even more desirably at least about 750 cubic centimeters per minute for improved performance. For example, the absorbent articles may define a Dry Air Exchange Rate of from about 525 to about 2500 cubic centimeters per minute and desirably from about 575 to about 2500 cubic centimeters per minute. Absorbent articles which exhibit Dry Air Exchange Rates less than those above do not allow a sufficient amount of air exchange and undesirably result in increased levels of skin hydration. Such increased levels of skin hydration can render the skin more susceptible to the growth of microorganisms which can undesirably lead to an increase in the incidence of skin irritation and rash.

The absorbent articles of the different aspects of the present invention may further be constructed to define a Wet Air Exchange Rate/Dry Air Exchange Rate ratio of at least about 0.20, generally at least about 0.23, desirably at least about 0.27, and more desirably at least about 0.30 for improved performance. For example, the absorbent articles may define a Wet Air Exchange Rate/Dry Air Exchange Rate ratio of from about 0.20 to about 1 and desirably from about 0.23 to about 1 for improved performance.

The ability of the absorbent articles of the present invention to exhibit high levels of air exchange rate both when dry and when wet has led to reduced levels of skin hydration. The ability of an absorbent article to achieve a low level of skin hydration has, for the purposes of this application, been quantified as the Skin Hydration Value. As used herein, the term "Skin Hydration Value" refers to the value determined according to the Skin Hydration Test set forth below. In general, the Skin Hydration Value is determined by measuring the evaporative water loss on the skin of test subjects after wearing the wetted absorbent article for a set period of time. In particular embodiments, the absorbent articles of the different aspects of the present invention may be constructed to define a Skin Hydration Value of less than about 18 grams per square meter per hour, generally less than about 15 grams per square meter per hour, desirably less than about 12 grams per square meter per hour, more desirably less than about 10 grams per square meter per hour, even more desirably less than about 8 grams per square meter per hour, and yet even more desirably less than about 5 grams per square meter per hour for improved performance. For example, the absorbent articles of the present invention may define a Skin Hydration Value of from about 0.1 to about 18 grams per square meter per hour and desirably from about 0.1 to about 12 grams per square meter per hour. Absorbent articles which exhibit Skin Hydration Values greater than those above can render the skin more susceptible to the growth of microorganisms which can undesirably lead to an increase in the incidence of skin irritation and rash.

The absorbent articles of the present invention may further exhibit reduced viability rates of microorganisms which can lead to a reduction in skin irritation. It is hypothesized that the reduced viability of microorganisms is a direct result of the increased breathability and air exchange within the articles of the present invention. The ability of an absorbent article to achieve a low rate of viability of microorganisms has, for the purposes of this application, been quantified as the *C. albicans* viability value since it is hypothesized that the presence of *Candida albicans* is directly related to the incidence of irritation and, in particular, rash. As used herein, the term "*C. albicans* viability" refers to the value determined according to the *Candida albicans* Viability Test set forth below. The *Candida albicans* Viability Test, in general, is a comparison of the *C. albicans* viability under a patch of the test absorbent article to the *C. albicans* viability under a control patch from a conventional absorbent article having a nonbreathable outer cover, i.e. an outer cover having a WVTR of less than 100 grams per square meter per 24 hours.

In particular embodiments, the absorbent articles of the different aspects of the present invention may be constructed to define a *C. albicans* viability of less than about 85 percent, generally less than about 80 percent, desirably less than about 60 percent, more desirably less than about 40 percent, and even more desirably less than about 20 percent of the *C. albicans* viability of the control for improved performance. For example, the absorbent articles of the present invention may define a *C. albicans* viability of less than about 2.5, desirably less than about 2.0, and more desirably less than about 1.75 log of *C. albicans* colony forming units when innoculated with a suspension of about 5–7 log of *C. albicans* colony forming units according to the *Candida albicans* Viability Test. Absorbent articles which exhibit *C. albicans* viability values greater than those above can undesirably lead to an increase in the incidence of skin irritation and rash. Desirably, the above *C. albicans* viability values are obtained without the incorporation of antimicrobial agents into the absorbent articles which can be perceived by consumers in a negative manner.

It has been discovered that acceptable, improved performance of absorbent articles can be achieved by selecting constructions having a combination of one or more of the above-described properties. For example, a given level of acceptable, improved performance may be achieved by employing an absorbent article which exhibits a Dry Air Exchange Rate of at least about 525 cubic centimeters per minute and a Wet Air Exchange Rate of at least about 175 cubic centimeters per minute, and desirably a Dry Air Exchange Rate of at least about 675 cubic centimeters per minute and a Wet Air Exchange Rate of at least about 200 cubic centimeters per minute. Alternatively, improved performance can be achieved by employing an absorbent article which exhibits a Wet Air Exchange Rate of at least about 175 cubic centimeters per minute and a Skin Hydration Value of less than about 18 grams per square meter per hour, and desirably a Wet Air Exchange Rate of at least about 200 cubic centimeters per minute and a Skin Hydration Value of less than about 12 grams per square meter per hour.

Still further, it has been discovered that improved performance can be achieved by employing absorbent articles having a Dry Air Exchange Rate of at least about 525 cubic centimeters per minute and a Wet Air Exchange Rate/Dry Air Exchange Rate ratio of at least about 0.20 and desirably a Dry Air Exchange Rate of at least about 625 cubic centimeters per minute and a Wet Air Exchange Rate/Dry Air Exchange Rate ratio of at least about 0.23.

Figure 2:
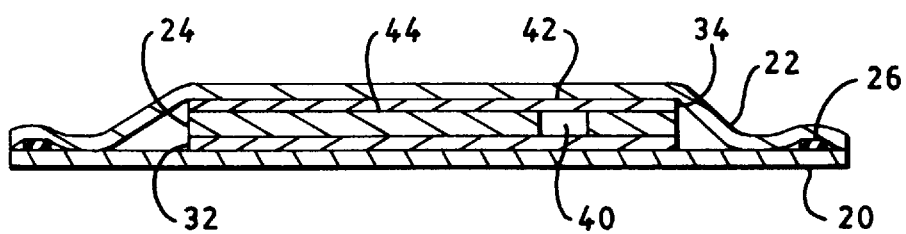
FIG. 2 representatively shows a sectional view of the absorbent article of FIG. 1 taken along line 2—2.

Examples of suitable constructions of absorbent articles for use in the present invention are described below and representatively illustrated in FIGS. 1–6. FIG. 1 is a representative plan view of an integral absorbent garment article, such as disposable diaper 10, of the present invention in its flat-out, uncontracted state (i.e., with all elastic induced gathering and contraction removed). Portions of the structure are partially cut away to more clearly show the interior construction of diaper 10, and the surface of the diaper which contacts the wearer is facing the viewer. FIG. 2 representatively shows a sectional view of the absorbent article of FIG. 1 taken along line 2—2. With reference to FIGS. 1 and 2, the disposable diaper 10 generally defines a front waist section 12, a rear waist section 14, and an intermediate section 16 which interconnects the front and rear waist sections. The front and rear waist sections include the general portions of the article which are constructed to extend substantially over the wearer's front and rear abdominal regions, respectively, during use. The intermediate section of the article includes the general portion of the article which is constructed to extend through the wearers crotch region between the legs.

The absorbent article includes a vapor permeable backsheet 20, a liquid permeable topsheet 22 positioned in facing relation with the backsheet 20, and an absorbent body 24, such as an absorbent pad, which is located between the backsheet 20 and the topsheet 22. The backsheet 20 defines a length and a width which, in the illustrated embodiment, coincide with the length and width of the diaper 10. The absorbent body 24 generally defines a length and width which are less than the length and width of the backsheet 20, respectively. Thus, marginal portions of the diaper 10, such as marginal sections of the backsheet 20, may extend past the terminal edges of the absorbent body 24. In the illustrated embodiments, for example, the backsheet 20 extends outwardly beyond the terminal marginal edges of the absorbent body 24 to form side margins and end margins of the diaper 10. The topsheet 22 is generally coextensive with the backsheet 20 but may optionally cover an area which is larger or smaller than the area of the backsheet 20, as desired. The backsheet 20 and topsheet 22 are intended to face the garment and body of the wearer, respectively, while in use.

The permeability of the backsheet is configured to enhance the breathability of the absorbent article to reduce the hydration of the wearer's skin during use without allowing excessive condensation of vapor, such as urine, on the garment facing surface of the backsheet 20 which can undesirably dampen the wearer's clothes.

To provide improved fit and to help reduce leakage of body exudates from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIGS. 1 and 2, the diaper 10 may indude leg elastics 26 which are constructed to operably gather and shirr the side margins of the diaper 10 to provide elasticized leg bands which can closely fit around the legs of the wearer to reduce leakage and provide improved comfort and appearance. Similarly, waist elastics 28 can be employed to elasticize the end margins of the diaper 10 to provide elasticized waists. The waist elastics are configured to operably gather and shirr the waist sections to provide a resilient, comfortably close fit around the waist of the wearer. In the illustrated embodiments, the elastic members are illustrated in their uncontracted, stretched condition for the purpose of clarity.

Fastening means, such as hook and loop fasteners 30, are employed to secure the diaper on a wearer. Alternatively, other fastening means, such as buttons, pins, snaps, adhesive tape fasteners, cohesives, mushroom-and-loop fasteners, or the like, may be employed.

The diaper 10 may further include other layers between the absorbent body 24 and the topsheet 22 or backsheet 20. For example, as representatively illustrated in FIGS. 1 and 2, the diaper 10 may include a ventilation layer 32 located between the absorbent body 24 and the backsheet 20 to insulate the backsheet 20 from the absorbent body 24 to improve air circulation and effectively reduce the dampness of the garment facing surface of the backsheet 20. The ventilation layer 32 may also assist in distributing fluid exudates to portions of the absorbent body 24 which do not directly receive the insult. The diaper 10 may also include a surge management layer 34 located between the topsheet 22 and the absorbent body 24 to prevent pooling of the fluid exudates and further improve air exchange and distribution of the fluid exudates within the diaper 10.

The diaper 10 may be of various suitable shapes. For example, the diaper may have an overall rectangular shape, T-shape or an approximately hourglass shape. In the shown embodiment, the diaper 10 has a generally I-shape. The diaper 10 further defines a longitudinal direction 36 and a lateral direction 38. Other suitable diaper components which may be incorporated on absorbent articles of the present invention include containment flaps, waist flaps, elastomeric side panels, and the like which are generally known to those skilled in the art.

Examples of diaper configurations suitable for use in connection with the instant application which may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bemardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 10 are integrally assembled together employing various types of suitable attachment means, such as adhesive, sonic bonds, thermal bonds or combinations thereof. In the shown embodiment, for example, the topsheet 22 and backsheet 20 are assembled to each other and to the absorbent body 24 with lines of adhesive, such as a hot melt, pressure-sensitive adhesive. Similarly, other diaper components, such as the elastic members 26 and 28, fastening members 30, and ventilation and surge layers 32 and 34 may be assembled into the diaper article by employing the above-identified attachment mechanisms.

The backsheet 20 of the diaper 10, as representatively illustrated in FIGS. 1 and 2, is composed of a substantially vapor permeable material. The backsheet 20 is generally constructed to be permeable to at least water vapor and has a water vapor transmission rate of at least about 1000 g/sq.m/24 hr., desirably at least about 1500 g/sq.m/24 hr, more desirably at least about 2000 g/sq.m/24 hr., and even more desirably at least about 3000 g/sq.m/24. For example, the backsheet 20 may define a water vapor transmission rate of from about 1000 to about 6000 g/sq.m/24 hr. Materials which have a water vapor transmission rate less than those above do not allow a sufficient amount of air exchange and undesirably result in increased levels of skin hydration.

The backsheet 20 is also desirably substantially liquid impermeable. For example, the backsheet may be constructed to provide a hydrohead value of at least about 60 cm, desirably at least about 80 cm, and more desirably at least about 100 cm when subjected to the Hydrostatic Pressure Test. Materials which have hydrohead values less than those above undesirably result in the strike through of liquids, such as urine, during use. Such fluid strike through can undesirably result in a damp, clammy feeling on the backsheet 20 during use.

The backsheet 20 may be composed of any suitable materials which either directly provide the above desired levels of liquid impermeability and air permeability or, in the alternative, materials which can be modified or treated in some manner to provide such levels. In one embodiment, the backsheet 20 may be a nonwoven fibrous web constructed to provide the required level of liquid impermeability. For example, a nonwoven web composed of spunbonded or meltblown polymer fibers may be selectively treated with a water repellent coating or laminated with a liquid impermeable, vapor permeable polymer film to provide the backsheet 20. In a particular embodiment of the invention, the backsheet 20 may comprise a nonwoven web composed of a plurality of randomly deposited hydrophobic thermoplastic meltblown fibers which are sufficiently bonded or otherwise connected to one another to provide a substantially vapor permeable and substantially liquid impermeable web. The backsheet 20 may also comprise a vapor permeable nonwoven layer which has been partially coated or otherwise configured to provide liquid impermeability in selected areas.

Examples of suitable materials for the backsheet 20 are also described in U.S. Pat. No. 5,482,765 issued Jan. 9, 1996 in the name of Bradley et al. and entitled "NONWOVEN FABRIC LAMINATE WITH ENHANCED BARRIER PROPERTIES"; U.S. patent application Ser. No. 08/622,903 filed Mar. 29, 1996 in the name of Odorzynski et al. and entitled "ABSORBENT ARTICLE HAVING A BREATHABILITY GRADIENT"; U.S. patent application Ser. No. 08/668,418 filed Jun. 21, 1996, in the name of Good et al. and entitled "ABSORBENT ARTICLE HAVING A COMPOSITE BREATHABLE BACKSHEET"; and U.S. patent application Ser. No. 08/882,712 filed Jun. 25, 1997, in the name of McCormack et al. and entitled "LOW GAUGE FILMS AND FILM/NONWOVEN LAMINATES", the disclosures of which are herein incorporated by reference.

In a particular embodiment, the backsheet 20 is provided by a microporous film/nonwoven laminate material comprising a spunbond nonwoven material laminated to a microporous film. The spunbond nonwoven comprises filaments of about 1.8 denier extruded from a copolymer of ethylene with about 3.5 weight percent propylene and defines a basis weight of from about 17 to about 25 grams per square meter. The film comprises a cast coextruded film having calcium carbonate particles therein and defines a basis weight of about 58 grams per square meter prior to stretching. The film is preheated, stretched and annealed to form the micropores and then laminated to the spunbond nonwoven. The resulting microporous film/nonwoven laminate based material has a basis weight of from about 30 to about 60 grams per square meter and a water vapor transmission rate of from about 3000 to about 6000 g/sq.m/24 hr. Examples of such film/nonwoven laminate materials are described in more detail in U.S. patent application Ser. No. 08/882,712 filed Jun. 25, 1997, in the name of McCormack et al. and entitled "LOW GAUGE FILMS AND FILM/NONWOVEN LAMINATES", the disclosure of which has been incorporated by reference.

The topsheet 22, as representatively illustrated in FIGS. 1 and 2, suitably presents a bodyfacing surface which is compliant, soft feeling, and nonirritating to the wearer's skin. Further, the topsheet 22 may be less hydrophilic than the absorbent body 24, to present a relatively dry surface to the wearer, and may be sufficiently porous to be liquid permeable, permitting liquid to readily penetrate through its thickness. A suitable topsheet 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 22 is suitably employed to help isolate the wearer's skin from liquids held in the absorbent body 24.

Various woven and nonwoven fabrics can be used for the topsheet 22. For example, the topsheet may be composed of a meltblown or spunbonded web of polyolefin fibers. The topsheet may also be a bondedcarded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 22 comprises a nonwoven, spunbond, polypropylene fabric composed of about 2.8–3.2 denier fibers formed into a web having a basis weight of about 22 grams per square meter and a density of about 0.06 gram per cubic centimeter. Such a topsheet 22 may be surface treated with an effective amount of a surfactant, such as about 0.3 weight percent of a surfactant commercially available from Hodgson Textile Chemicals Co. under the trade designauon AHCOVEL BASE N-62.

The absorbent body 24 of the diaper 10, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent body 24 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. Alternatively, the absorbent body 24 may comprise a laminate of fibrous webs and superabsorbent material or other suitable means of maintaining a superabsorbent material in a localized area.

The absorbent body 24 may have any of a number of shapes. For example, the absorbent core may be rectangular, I-shaped, or T-shaped. It is generally preferred that the absorbent body 24 be narrower in the intermediate section than in the front or rear waist sections of the diaper 10. The absorbent body 24 may be provided by a single layer or, in the alternative, may be provided by multiple layers, all of which need not extend the entire length and width of the absorbent body 24. In a particular aspect of the invention, the absorbent body 24 can be generally T-shaped with the laterally extending cross-bar of the "T" generally corresponding to the front waist section 12 of the absorbent article for improved performance, especially for male infants. In the illustrated embodiments, for example, the absorbent body 24 across the front waist section 12 of the article has a cross-directional width of about 18 centimeters, the narrowest portion of the intermediate section 16 has a width of about 7.5 centimeters and in the rear waist section 14 has a width of about 11.4 centimeters.

The size and the absorbent capacity of absorbent body 24 should be compatible with the size of the intended wearer and the liquid loading imparted by the intended use of the absorbent article. Further, the size and the absorbent capacity of the absorbent body 24 can be varied to accommodate wearers ranging from infants through adults. In addition, it has been found that with the present invention, the densities and/or basis weights of the absorbent body 24 can be varied.

In a particular aspect of the invention, the absorbent body 24 has an absorbent capacity of at least about 300 grams of synthetic urine.

In embodiments wherein the absorbent body 24 includes the combination of hydrophilic fibers and high-absorbency particles, the hydrophilic fibers and high-absorbency particles can form an average basis weight for the absorbent body 24 which is within the range of about 400–900 grams per square meter. In certain aspects of the invention, the average composite basis weight of such an absorbent body 24 is within the range of about 500–800 grams per square meter, and preferably is within the range of about 550–750 grams per square meter to provide the desired performance.

To provide the desired thinness dimension to the various configurations of the absorbent article of the invention, the absorbent body 24 can be configured with a bulk thickness which is not more than about 0.6 centimeters. Preferably, the bulk thickness is not more than about 0.53 centimeters, and more preferably is not more than about 0.5 centimeters to provide improved benefits. The bulk thickness is determined under a restraining pressure of 0.2 psi (1.38 kPa).

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. In general, the high absorbency material is present in the absorbent body in an amount of from about 5 to about 90 weight percent, desirably in an amount of at least about 30 weight percent, and even more desirably in an amount of at least about 50 weight percent based on a total weight of the absorbent body 24. For example, in a particularly embodiment, the absorbent body 24 may comprise a laminate which includes at least about 50 weight percent and desirably at least about 70 weight percent of high-absorbency material overwrapped by a fibrous web or other suitable means of maintaining the high-absorbency material in a localized area.

An example of high-absorbency material suitable for use in the present invention is SANWET IM 3900 polymer available from Hoechst Celanese, a business having offices in Portsmouth, Va. Other suitable superabsorbents may include W45926 or FAVOR SXM 880 polymer obtained from Stockhausen, a business having offices in Greensboro, N.C.

Optionally, a substantially hydrophilic tissue wrapsheet (not illustrated) may be employed to help maintain the integrity of the structure of the absorbent body 24. The tissue wrap sheet is typically placed about the absorbent body over at least the two major facing surfaces thereof and composed of an absorbent cellulosic material, such as creped wadding or a high wet-strength tissue. In one aspect of the invention, the tissue wrap can be configured to provide a wicking layer which helps to rapidly distribute liquid over the mass of absorbent fibers comprising the absorbent body.

The absorbent body 24 of the different aspects of the present invention further includes a plurality of zones of high air permeability which allow air and vapors to readily pass through the absorbent body 24 and through the vapor permeable backsheet 20 out of the diaper 10 into ambient air. For example, as representatively illustrated in FIGS. 1 and 2, the absorbent body 24 may include a plurality of air passageways 40 which provide the absorbent body 24 with the zones or regions of high air permeability 42. In the illustrated embodiment, the portions of the absorbent body 24 adjacent the air passageways 40 provide zones or regions of high absorption 44. The zones of high air permeability 42 are designed to provide the maximum air exchange from the absorbent body 24 while the zones of high absorption 44 are designed to receive and hold the majority of the body exudates. The absorbent body 24 may define any number of zones of high air permeability 42 which provides the improved air exchange. Desirably, the absorbent body 24 defines at least 3 and more desirably at least 5 different zones of high air permeability 42 for improved performance.

The zones of high air permeability 42, such as the air passageways 40 as representatively illustrated in FIGS. 1 and 2, are configured to enhance the breathability of the article to reduce the hydration of the wearer's skin during use without allowing excessive condensation of vapor, such as urine, on the garment facing surface of the backsheet 20. Such condensation of vapor on the outer surface of the diaper 10 can undesirably dampen the wearer's clothes. The zones of high air permeability 42 are generally located in the area of the diaper over which air and vapor can transfer from the topsheet 22, through the absorbent body 24 and any other intervening layer or layers of material, and out the vapor permeable backsheet 20. For example, the zones of high air permeability 42 may be located throughout the entire absorbent body 24 or may be selectively located in those regions of the absorbent body 24 which provide the maximum air exchange, such as the intermediate section 16 of the diaper 20. In a particular embodiment, the zones of high air permeability 42 are located in the front and intermediate sections 12 and 16, respectively, of the diaper 10 for improved air exchange.

The zones of high absorption 44, on the other hand, are not designed to transfer a high level of air and vapor from the interior of the diaper. Thus, the air exchange from the topsheet 22 of the diaper 10 to the backsheet 20 of the diaper and into the ambient atmosphere (exterior of the diaper) occurs generally through the absorbent body 24 in the zones of high air permeability 42. Some air exchange through the absorbent body 24 can also occur in the zones of high absorption 44 to a limited degree.

The zones of high air permeability may have any desired configuration including rectangular, circular, hourglass, oval, and the like, and may also include selected longitudinal or lateral strips or multiple regions which may be intermittently located. For example, in FIGS. 1 and 2, the zones of high air permeability 42 are provided by a plurality of air passageways 40 or apertures through the absorbent body 24 which have a generally circular configuration. In such a configuration, the zones of high absorption 44 comprise the non-apertured portions of the absorbent body 24 between the air passageways 40.

The zones of high air permeability 42 may have any desired dimensions which effectively provide improved air exchange while preventing excessive condensation of vapor from the absorbent body 24 through and onto the garment facing surface of the backsheet 20. Desirably, the zones of high air permeability 42 may define a total area of from about 5 to about 75 percent, more desirably at least about 10 percent, even more desirably from about 10 to about 70 percent, and still more desirably from about 10 to about 60 percent of the total surface area of the absorbent body 24 of the diaper 10. For example, in a diaper intended for use on a medium sized infant, the zones of high air permeability 42 may define a total area of from about 6 to about 90 square centimeters.

When the total area of the zones of high air permeability 42 is greater than the above amounts, the diaper 10 may exhibit an undesirable amount of condensation of vapor on the exposed, garment facing surface of the backsheet 20 undesirably resulting in a clammy feeling on the outer surface of the diaper. Whereas, when the total area of the zones of high air permeability 42 is less than the above amounts, the diaper 10 may exhibit a low level of air exchange resulting in high levels of skin hydration which can undesirably lead to skin irritation and rash.

The zones of high air permeability 42 of the absorbent body 24 of the diaper 10, as representatively illustrated in FIGS. 1 and 2, are constructed to be substantially permeable to at least air and preferably permeable to water vapor. For example, the zones of high air permeability 42 of the absorbent body 24 define a Frazier Porosity value which is at least about 10 percent, more desirably at least about 20 percent and even more desirably at least about 50 percent greater than the Frazier Porosity value of the zones of high absorption 44 of the absorbent body 24. As used herein, the term "Frazier Porosity" refers to the value determined according to the Frazier Porosity Test set forth below. When the zones of high air permeability exhibit Frazier Porosity values less than those indicated above, the diaper 10 may exhibit a low level of air exchange resulting in high levels of skin hydration which can undesirably lead to skin irritation and rash.

The zones of high air permeability may be provided in a variety of ways. The zones of high air permeability 42 may be integral portions of the absorbent body 24 of the absorbent article or may be provided by apertures, holes or open spaces in the absorbent body 24. For example, portions of the absorbent body 24 may be discontinuous or removed to provide the zones 42. Alternatively, the zones of high air permeability 42 may be provided by portions of the absorbent body 24 which are constructed to absorb less fluid exudates thereby resulting in improved air flow through such portions in use. For example, portions of the absorbent body 24 may be void of or contain substantially less high-absorbency material than other portions of the absorbent body 24 to provide such improved air flow. Portions of the absorbent body 24 may otherwise be treated or coated with a solution which renders them hydrophobic to provide the zones of high air permeability 42 in selected areas. In other alternative configurations, the zones of high air permeability 42 may be provided by creating voids or holes in the absorbent body 24 and placing other materials having a higher air permeability than the absorbent body 24, such as those materials described below as being suitable for the surge management layer 34, in the holes or voids.

Examples of several configurations of the absorbent body 24 according to different aspects of the present invention are representatively illustrated in FIGS. 1–6. For example, in FIGS. 1 and 2, the zones of high air permeability 42 in the absorbent body 24 are provided by a plurality of air passageways 40 or apertures through the absorbent body 24. In the illustrated embodiment, the air passageways 40 are intermittently positioned along the entire length and width of the absorbent body 24. The illustrated air passageways 40 are circular and define a diameter of about 1.27 centimeters and a total open area of about 12 percent of a total surface area of the absorbent body 24.

Figure 3:
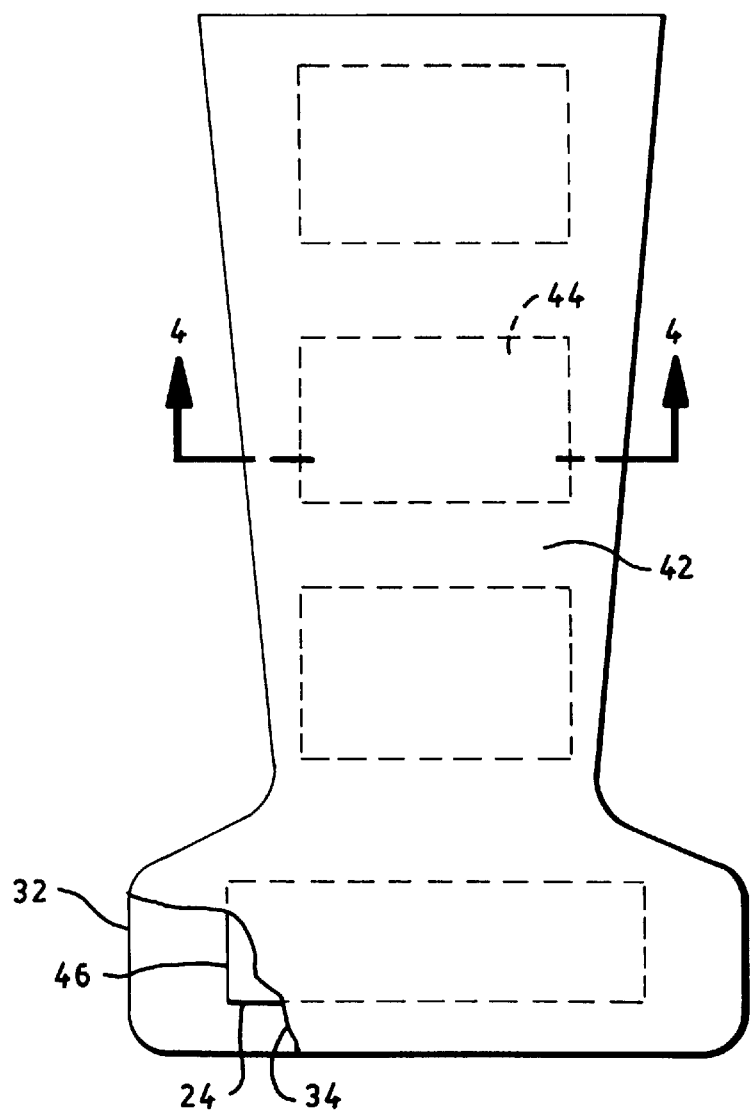
FIG. 3 representatively shows a partially cutaway, top plan view of an absorbent body for an absorbent article according to another embodiment of the invention.
Figure 4:
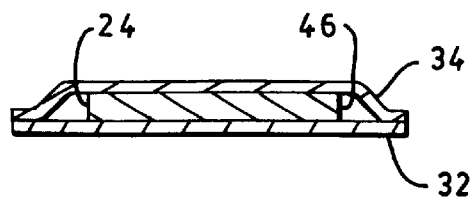
FIG. 4 representatively shows a sectional view of the absorbent body of FIG. 3 taken along line 4—4.

In FIGS. 3 and 4, the absorbent body 24 is in the form of discrete segments 46 which are spaced apart along the longitudinal direction 36 of the diaper 10. In such a configuration, the zones of high air permeability 42 are provided by the spaces between the discrete segments 46 of the absorbent body 24. The absorbent body 24 may include any number of segments 46 having a variety of shapes and sizes. For example, in the illustrated embodiment, the absorbent body 24 includes four different segments 46 spaced apart in the longitudinal direction 36 of the diaper 10. The illustrated segments 46 are generally rectangular in shape and define a width which is less than a width of the absorbent body 24 which, in the illustrated embodiment, is defined by the width of the surge management layer 34 and the ventilation layer 32 as described below. Alternatively, the segments 46 may define a width which is substantially equal to a width of the absorbent body 24. To assist in maintaining the segments 46 in the spaced apart relationship, the segments 46 can be contained between two sheets of material such as wrapsheet (not shown) or the surge management layer 34 and the ventilation layer 32. In the illustrated embodiment, the segments 46 include a laminate of high-absorbency material between two sheets or layers of material and the zones of high air permeability 42 provided by the spaces between the segments 46 define an open area of about 40 percent of a total surface are of the absorbent body 24.

Figure 5:
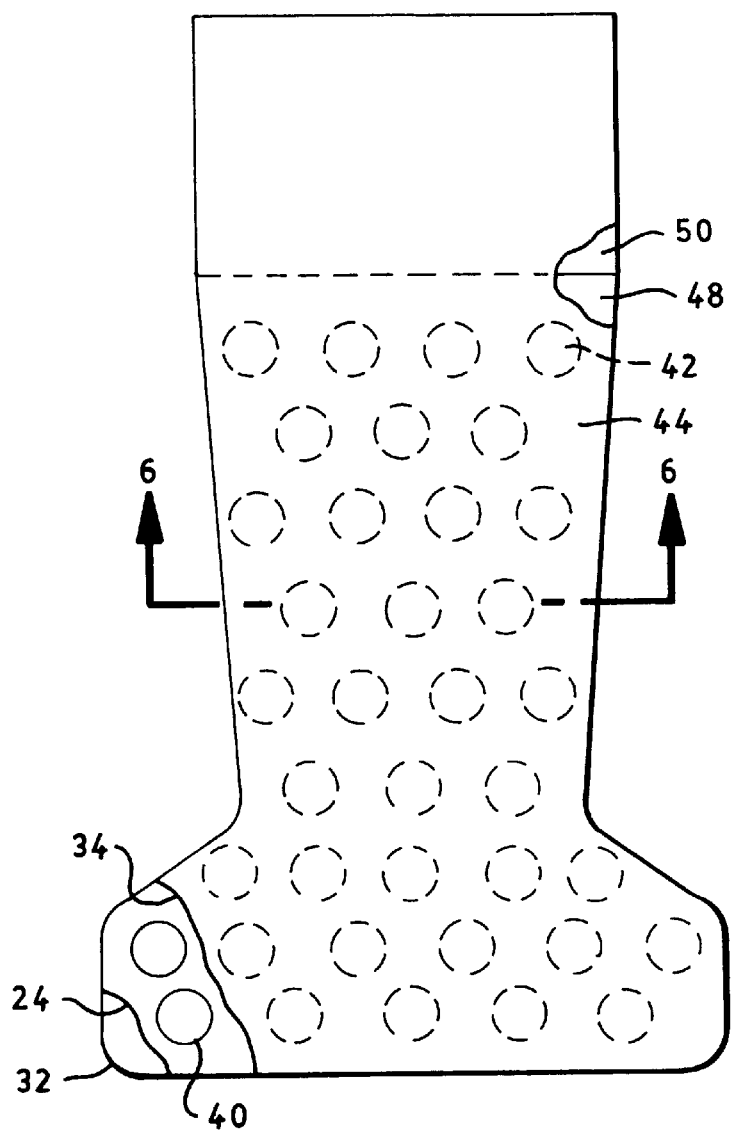
FIG. 5 representatively shows a partially cutaway, top plan view of an absorbent body for an absorbent article according to another embodiment of the invention.
Figure 6:
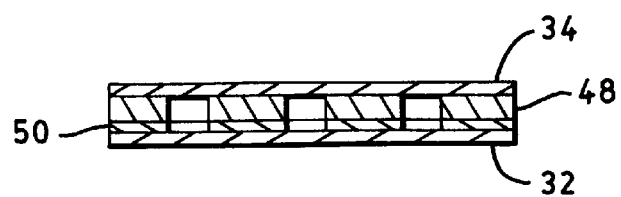
FIG. 6 representatively shows a sectional view of the absorbent body of FIG. 5 taken along line 6—6.

In FIGS. 5 and 6, the zones of high air permeability 42 in the absorbent body 24 are provided by a plurality of air passageways 40 or apertures through the absorbent body 24 similar to the embodiment illustrated in FIGS. 1 and 2. However, in the embodiment illustrated in FIGS. 5 and 6, the air passageways 40 are located in the absorbent body 24 in the front waist section 12 and the intermediate section 16 of the diaper 10 and not in the rear waist section 14. Moreover, in the embodiment illustrated in FIGS. 5 and 6, the absorbent body 24 includes an upper layer 48 and a lower layer 50 with the upper layer 48 extending only along a portion of the length of the absorbent body 24. In such a configuration, the majority of the absorbent body 24 can be located in the front waist and intermediate sections 12 and 16 of the diaper 10 for improved absorption and reduced cost. The illustrated air passageways 40 are circular and define a diameter of about 1.27 centimeters and a total open area of about 12 percent of a total surface area of the absorbent body 24.

Due to the thinness of absorbent body 24 and the high absorbency material within the absorbent body 24, the liquid uptake rates of the absorbent body 24, by itself, may be too low, or may not be adequately sustained over multiple insults of liquid into the absorbent body 24. To improve the overall liquid uptake and air exchange, the diaper of the different aspects of the present invention may further include a porous, liquid-permeable layer of surge management material 34, as representatively illustrated in FIGS. 1 and 2. The surge management layer 34 is typically less hydrophilic than the absorbent body 24, and has an operable level of density and basis weight to quickly collect and temporarily hold liquid surges, to transport the liquid from its initial entrance point and to substantially completely release the liquid to other parts of the absorbent body 24. This configuration can help prevent the liquid from pooling and collecting on the portion of the absorbent garment positioned against the wearer's skin, thereby reducing the feeling of wetness by the wearer. The structure of the surge management layer 34 also generally enhances the air exchange within the diaper 10.

Various woven and nonwoven fabrics can be used to construct the surge management layer 34. For example, the surge management layer 34 may be a layer composed of a meltblown or spunbonded web of synthetic fibers, such as polyolefin fibers. The surge management layer 34 may also be a bonded-carded-web or an airlaid web composed of natural and synthetic fibers. The bonded-carded-web may, for example, be a thermally bonded web which is bonded using low melt binder fibers, powder or adhesive. The webs can optionally include a mixture of different fibers. The surge management layer 34 may be composed of a substantially hydrophobic material, and the hydrophobic material may optionally be treated with a surfactant or otherwise processed to impart a desired level of wettability and hydrophilicity. In a particular embodiment, the surge management layer 34 includes a hydrophobic, nonwoven material having a basis weight of from about 30 to about 120 grams per square meter.

For example, in a particular embodiment, the surge management layer 34 may comprise a bonded-carded-web, nonwoven fabric which includes bicomponent fibers and which defines an overall basis weight of about 83 grams per square meter. The surge management layer 34 in such a configuration can be a homogeneous blend composed of about 60 weight percent polyethylene/polyester (PE/PET), sheath-core bicomponent fibers which have a fiber denier of about 3 d and about 40 weight percent single component polyester fibers which have a fiber denier of about 6 d and which have fiber lengths of from about 3.8 to about 5.08 centimeters.

In the illustrated embodiments, the surge management layer 34 is arranged in a direct, contacting liquid communication with the absorbent body 24. The surge management layer 34 may be operably connected to the topsheet 22 with a conventional pattern of adhesive, such as a swirl adhesive pattern. In addition, the surge management layer 34 may be operably connected to the absorbent body 24 with a conventional pattern of adhesive. The amount of adhesive add-on should be sufficient to provide the desired levels of bonding, but should be low enough to avoid excessively restricting the movement of liquid from the topsheet 22, through the surge management layer 34 and into the absorbent body 24.

The absorbent body 24 is positioned in liquid communication with surge management layer 34 to receive liquids released from the surge management layer, and to hold and store the liquid. In the shown embodiments, the surge management layer 34 comprises a separate layer which is positioned over another, separate layer comprising the absorbent body 24, thereby forming a dual-layer arrangement. The surge management layer 34 serves to quickly collect and temporarily hold discharged liquids, to transport such liquids from the point of initial contact and spread the liquid to other parts of the surge management layer 34, and then to substantially completely release such liquids into the layer or layers comprising the absorbent body 24.

The surge management layer 34 can be of any desired shape. Suitable shapes include for example, circular, rectangular, triangular, trapezoidal, oblong, dog-boned, hourglass-shaped, or oval. In certain embodiments, for example, the surge management layer can be generally rectangular-shaped. In the illustrated embodiments, the surge management layer 34 is coextensive with the absorbent body 24. Alternatively, the surge management layer 34 may extend over only a part of the absorbent body 24. Where the surge management layer 34 extends only partially along the length of the absorbent body 24, the surge management layer 34 may be selectively positioned anywhere along the absorbent body 24. For example, the surge management layer 34 may function more efficiently when it is offset toward the front waist section 12 of the garment. The surge management layer 34 may also be approximately centered about the longitudinal center line of the absorbent body 24.

Additional materials suitable for the surge management layer 34 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

As representatively illustrated in FIGS. 1 and 2, the diaper 10 may also include a ventilation layer 32 located between the backsheet 20 and the absorbent body 24. The ventilation layer 32 serves to facilitate the movement of air within and through the diaper 10 and prevent the backsheet 20 from being in surface to surface contact with at least a portion of the absorbent body 24. Specifically, the ventilation layer 32 serves as a conduit through which air and water vapor can move from the absorbent body 24 through the vapor permeable backsheet 20.

The ventilation layer 32 may be formed from materials described above as being suitable for the surge management layer 34 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material or a composite of two or more layers of material. In a particular embodiment, the ventilation layer 32 includes a hydrophobic, nonwoven material having a thickness of at least about 0.10 centimeters determined under a restraining pressure of 0.05 psi (0.34 kPa) and a basis weight of from about 20 to about 120 grams per square meter. For example, the ventilation layer 32 may comprise a bonded-carded-web, nonwoven fabric which includes bicomponent fibers and which defines an overall basis weight of about 83 grams per square meter. The ventilation layer 32 in such a configuration can be a homogeneous blend composed of about 60 weight percent polyethylene/ polyester (PE/PET), sheath-core bicomponent fibers which have a fiber denier of about 3 d and about 40 weight percent single component polyester fibers which have a fiber denier of about 6 d and which have fiber lengths of from about 3.8 to about 5.08 centimeters.

The ventilation layer 32 can be of any desired shape. Suitable shapes include for example, circular, rectangular, triangular, trapezoidal, oblong, dog-boned, hourglass-shaped, or oval. The ventilation layer 32 may extend beyond, completely over or partially over the absorbent body 24. For example, the ventilation layer 32 may suitably be located over the intermediate section 16 of the diaper 10 and be substantially centered side-to-side with respect to the longitudinal centerline 36 of the diaper 10. It is generally desired that the entire absorbent body 24 be overlaid with the ventilation layer 32 to prevent substantially all surface to surface contact between the backsheet 20 and the absorbent body 24. In the illustrated embodiments, the ventilation layer 32 is coextensive with the absorbent body 24. This allows for the maximum degree of air exchange with minimal dampness on the garment facing surface of the backsheet 20.

In the illustrated embodiments, the ventilation layer 32 is arranged in a direct, contacting liquid communication with the absorbent body 24. The ventilation layer 32 may be operably connected to the backsheet 20 with a conventional pattern of adhesive, such as a swirl adhesive pattern. In addition, the ventilation layer 32 may be operably connected to the absorbent body 24 with a conventional pattern of adhesive. The amount of adhesive add-on should be sufficient to provide the desired levels of bonding, but should be low enough to avoid excessively restricting the movement of air and vapor from the absorbent body 24 and through the backsheet 20.

The ventilation layer 32 may further serve to quickly collect and temporarily hold discharged liquids, which pass through the absorbent body 24 and, in particular, through the zones of high air permeability 42 within the absorbent body 24. The ventilation layer 32 may then transport such liquids from the point of initial contact and spread the liquid to other parts of the ventilation layer 32, and then substantially completely release such liquids into the layer or layers comprising the absorbent body 24.

The different embodiments of the present invention, as representatively illustrated in FIGS. 1–6, advantageously provide improved absorbent articles which exhibit substantially reduced levels of hydration of the wearer's skin when in use compared to conventional absorbent articles. The reduced levels of skin hydration promote drier, more comfortable skin and render the skin less susceptible to the viability of microorganisms. Thus, wearer's of absorbent articles made according to the present invention have reduced skin hydration which can lead to a reduction in the incidence of skin irritation and rash.

TEST PROCEDURES

Hydrostatic Pressure Test

The Hydrostatic Pressure Test is a measure of the liquid barrier properties of a material. In general, the Hydrostatic Pressure Test determines the height of water (in centimeters) in a column which the material will support before a predetermined amount of water passes through. A material with a higher hydrohead value indicates it is a greater barrier to liquid penetration than a material having a lower hydrohead value. The Hydrostatic Pressure Test is performed according to Method 5514—Federal Test Methods Standard No. 191A.

Frazier Porosity Test

The Frazier Porosity values referred to in the present specification can be determined employing a Frazier Air Permeability Tester (Frazier Precision Instrument Co., Gaithersburg, Md.) and Method 5450, Federal Test Methods Standard No. 191A. For the purposes of the present invention, the test is conducted with a sample which measures 8 inches×8 inches.

Water Vapor Transmission Test

A suitable technique for determining the WVTR (water vapor transmission rate) value of a material is as follows. For the purposes of the present invention, 3-inch diameter (76 millimeter) circular samples are cut from the test material and from a control material, Celguard® 2500 (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test } WVTR = \frac{[(\text{grams weight loss over 24 hours}) \times 7571]}{24} \; (g/m^2/24 \text{ hours})$$

The relative humidity within the oven is not specifically controlled. Under predetermined set conditions of 100° F. and ambient relative humidity, the WVTR for Celguard 2500 has been determined to be 5000 g/m$^2$/24 hours. Accordingly, Celguard 2500 is run as a control sample with each test. Celguard 2500 is a 0.0025 cm thick film composed of a microporous polypropylene.

Skin Hydration Test

Skin hydration values are determined by measuring total evaporative water loss (EL) and can be determined by employing the following test procedure.

The test is conducted on partially toilet trained infants who have no lotions or ointments on the skin and have not been bathed within 2 hours prior to the test. Each infant tests one diaper during each test session. The test diapers include a test code and a control code. The test diapers (test code and control code) are randomized.

Each test diaper is weighed before and after use to verify the volume of liquid added into the diaper. A felt tip pen is employed to mark an "X" at the target zone inside the diaper, with the "X" positioned 6.5 inches below the top front edge of the diaper and centered side-to-side. The EL measurements are taken with an evaporimeter, such as an Evaporimeter EP1 instrument distributed by Servomed AB, Stockholm, Sweden. Each test measurement is taken over a period of two minutes with EWL values taken once per second (a total of 120 EWL values). The digital output from the Evaporimeter EP1 instrument gives the rate of evaporative water loss (EWL) in $g/m^2/hr$. Skin hydration values (SHV) are in units of total amount of water loss per unit area measured during the two-minute sampling period and are calculated as follows.

$$SHV(g/m^2/hour) = \frac{\sum_{n=1}^{120}(EWL)_n}{120}$$

A preliminary skin hydration value measurement is taken after a 15-minute "dryout" period when the infant wears only a long T-shirt or dress and is in the supine position. The measurement is taken on the infant's lower abdomen, in a region corresponding to the target zone of the diaper, using the evaporimeter for the purpose of establishing the initial skin hydration value of the infants skin at the diaper target zone. If the preliminary SHV is less than 10 $g/m^2/hour$, a diaper is then placed on the infant. If the preliminary SHV is greater than 10 $g/m^2/hour$, the "dryout" period is extended until a reading below 10 $g/m^2/hour$ is obtained. Prior to securing the diaper on the infant, a tube is positioned to direct a flow of liquid to hit the premarked target zone. Once the diaper is secured, 210 milliliters of adjusted 0.9 weight percent aqueous saline is added in three insults of 70 milliliters each at a rate of 15 milliliters/second with a 45 second delay between insults.

The infant wears the diaper for 60 minutes after which the diaper is removed and a test measurement of skin hydration is taken on the lower abdomen corresponding to the target zone mark of the diaper. The measurement is taken over a 2-minute period. The used diaper is then weighed. Relative humidity and temperature measurements can be taken within the diaper prior to the skin hydration measurements being taken. The test procedure is then repeated the next day for each infant using the diaper type (test or control) which the infant has not yet worn. The control diaper provides a standardized basis for comparing the performance of the diaper configuration being tested and evaluated. The control diapers used in the tests performed in connection with the Examples were commercially available HUGGIES® Supreme diapers sold by Kimberly-Clark Corporation.

Data is discarded for any infants which have added to the loading of saline solution. The value reported for the mean net SHV (grams/$m^2$ in one hour) is the arithmetic mean for all infants of the post-wear skin hydration value, taken at the lower abdomen (target zone mark), minus the skin hydration value measured at the lower abdomen prior to placing the diaper on the infant (after "dryout" period). A separate mean net SHV is determined for the test code diapers and the control code diapers.

The net skin hydration value is determined as follows:

Net $SHV_i = Y - Z$

Where:

Y=skin hydration value measured at target zone mark of an individual infant

Z=baseline skin hydration value measured on the lower abdomen after "dryout" period prior to placing diaper on the infant $SHV_i$=skin hydration value for individual infant Then, $$\text{Mean Net } SHV = \frac{\sum_{i=1}^{N} \text{Net } SHV_i}{N}$$

Where: N=number of infants in study

The percent reduction in skin hydration is determined as follows:

$$\% \text{ Reduction} = \frac{\sum_{i=1}^{N}[((C-D)/C) \times 100]}{N}$$

Where:
   C=Net $SHV_i$ for control diaper code
   D=Net $SHV_i$ for test diaper code
   N=number of infants in study Tracer Gas Test The Tracer Gas Test is a measure of the rate of air exchange in garments such as absorbent articles and is a steady flow/steady state test described generally in TAPPI JOURNAL., Volume 80, No. 9, September 1997. In general, the air exchange rate values are calculated from the measured mass exchange within the garment. The test involves injecting a tracer gas at a constant rate inside the article next to the outer surface of the torso of a mannequin while the article is secured about the mannequin. Simultaneously, the concentration of the tracer gas in the air space between the article and the mannequin is measured by withdrawing a sample at the same constant rate as the injection. The air exchange rate is then be determined based on mass balances of the tracer gas and the air within the space in question. The Tracer Gas Test is completed as follows:

Equipment

1. Mannequin—The test is conducted with Step 3 or Step 4 sized diapers designed for infants weighing from about 16 to about 28 pounds and from about 22 to about 37 pounds, respectively. The diapers are placed on mannequins which have the following dimensions:

| Step 3 | |
|---|---|
| height (waist to knees) | 26 centimeters |
| circumference at waist | 42 centimeters |
| circumference at hips | 44 centimeters |
| thigh circumference | 22 centimeters |
| Step 4 | |
| height (waist to knees) | 28 centimeters |
| circumference at waist | 45 centimeters |
| circumference at hips | 51 centimeters |
| thigh circumference | 27 centimeters |

2. A test area which is environmentally controlled to 20° C. and 50% relative humidity.

3. $CO_2$ Analyzer—An infrared $CO_2$ Analyzer auch as Model 17515A commercially available from Vacu-Med Vacumetrics, 4483 McGrath Street #102, Ventura, California.

4. Rotameters—Rotameters to maintain gas flow rates such as Matheson Rotameter Model TS-35 commercially available from Specialty Gases Southeast Inc., 3496 Peachtree Parkway, Suwanee, Ga.

5. Gas Cylinders—Two gas cylinders of calibrated medical grade gas at a pressure of 4 kPa from Specialty Gases Southeast Inc., 3496 Peachtree Parkway, Suwanee, Ga. The tracer gas includes 5% $CO_2$ and air and the calibration gas is 100% air.

Procedure

1. Turn the $CO_2$ analyzer on. After it has been on for 30 minutes, calibrate the analyzer with the calibration gas and adjust the flow control to achieve a flow rate of 150 cubic centimeters per minute through the analyzer.

2. Place the diaper to be tested on the mannequin.

3. Turn on the $CO_2$ tracer gas flow. The flow rate of the injected tracer gas into the space between the diaper and the mannequin must be equal to the sample flow rate through the $CO_2$ analyzer (150 cc/min.).

4. Measure and record the concentration (C) of the tracer gas ($CO_2$) in the air space between the diaper and the mannequin every 10 seconds for 20 minutes. The data over the last 10 minutes are averaged and used to calculate the air exchange rate as follows:

$$\text{Air Exchange Rate} = 150 \text{ cc/min} * [(C_T - C)/(C - C_O)]$$

wherein, $C_T$=concentration of the tracer gas (5%)

C=concentration of the tracer gas in the space being measured $C_O$=concentration of the tracer gas in the chamber environment (0.04%)

pThe Dry Air Exchange Rate is the air exchange rate as determined according to the above procedure before the diaper has been subjected to any insults. The Wet Air Exchange Rate is the air exchange rate determined according to the above procedure except that once the diaper is secured to the mannequin, 180 milliliters (Step 3) or 210 milliliters (Step 4) of adjusted 0.9 weight percent aqueous saline is added in three insults of 60 or 70 milliliters each at a rate of 15 milliliters/second with a 45 second delay between insults. The Wet Air Exchange Rate/Dry Air Exchange Rate ratio is determined by dividing the Wet Air Exchange Rate by the Dry Air Exchange Rate for the same sample.

C. albicans Viability Test

The C. albicans Viability Test is a measure of the effect of absorbent garments, such as disposable diapers, on the viability of pathogenic microorganisms and, in particular, Candida albicans. In general, the C. albicans Viability Test involves inoculating delineated sites of each volar forearm of test subjects with a known suspension of C. albicans cells, covering the sites with full thickness patch from the absorbent garment, and determining the viability after a 24 hour period.

A full thickness test sample patch having a length of about 5 centimeters and a width of about 5 centimeters is cut from the target zone of each product to be tested. The target zone is generally that portion of the product intended to receive urine discharge from the wearer and typically includes portions of the intermediate and front waist sections of the product somewhat forward of the lateral centerline of the product. In a typical diaper configuration, the full thickness test sample patch includes the topsheet, absorbent body, backsheet and any intervening layers. Approximately 15 milliliters of a 0.9 weight percent saline solution is added to the test sample patch and allowed to soak in for 2 minutes before the samples are placed on the forearms of the test subjects. A test site area of about 6.15 square centimeters is marked on each of the test subject's volar forearms. Approximately 0.01 milliliters of a 0.9 weight percent saline solution containing a known suspension of C. albicans cells is delivered to the test site with micropipettes and the suspension is then spread uniformly across the test site. After air drying, the test site is covered with the test sample patch which is secured in position using adhesive tape completely surrounding the sample.

After 24 hours, the test sample patches are removed and a quantitative culture is obtained from the test site using the detergent scrub method set forth in "A New Method For Quantitative Investigation of Cutaneous Bacteria", P. Williamson and A. M. Klingman, *Journal of Investigative Dermatology*, 45:498–503, 1965, the disclosure of which is hereby incorporated by reference. Briefly; a sterile glass cylinder encompassing an area of 6.15 square centimeters is centered over the test site and held firmly to the skin. One milliliter of 0.1 weight percent Triton-x-100 in 0.075M phosphate buffer having a pH of 7.9 is pipetted into the glass cylinder and the area scrubbed for one minute using a sterile Teflon rod. The fluid is aspirated with a sterile pipette and a second milliliter of 0.1 weight percent Triton-x-100 in 0.075M phosphate buffer having a pH of 7.9 is added to the glass cylinder. The scrub step is repeated and the two washes are pooled. Each pooled sample is diluted in ten-fold steps with of 0.05 weight percent Triton-x-100 in 0.0375M phosphate buffer having a pH of 7.9. A 0.01 milliliter aliquot of each dilution is inoculated onto Sabourands agar containing antibiotics. Duplicate cultures are prepared and incubated at room temperature for 48 hours.

After incubation, the number of colony forming units are counted using standard microbiological methods. The C. albicans viability under a patch of the test sample can then be compared to the C. albicans viability under a control patch from a conventional absorbent article having a non-breathable outer cover, i.e. an outer cover having a WVTR of less than 100 grams per square meter per 24 hours, such as the diaper described below in connection with Comparative Example 4.

The following examples are presented to provide a more detailed understanding of the invention. The specific materials and parameters are exemplary and are not intended to specifically limit the scope of the invention.

EXAMPLES

Example 1

Disposable diapers having the same general construction as the HUGGIES® Supreme Step 3 diapers described in connection with Comparative Example 2 below were hand made and tested. The diapers were substantially the same as the Supreme diapers except that the backsheet, absorbent core, surge layer and elasticized legbands of the diapers were replaced or modified and a ventilation layer was added between the backsheet and the absorbent core.

In the tested diapers, the backsheet included a microporous film/nonwoven laminate material comprising a spunbond nonwoven material laminated to a microporous film. The spunbond nonwoven comprised filaments of about 1.8 denier extruded from a copolymer of ethylene with about 3.5 weight percent propylene and defined a basis weight of from about 20 grams per square meter. The film comprised a cast coextruded film having calcium carbonate particles therein and defined a basis weight of about 58 grams per square meter prior to stretching. The film was preheated, stretched and annealed to form the micropores and then laminated to the spunbond nonwoven material. The resulting microporous film/nonwoven laminate based material had a basis weight of 45 grams per square meter and a water vapor transmission rate of about 4000 grams per square meter per 24 hours. Examples of such film/nonwoven laminate materials are described in more detail in U.S. patent application Ser. No. 08/882,712 filed Jun. 25, 1997, in the name of McCormack et al. and entitled "LOW GAUGE FILMS AND FILM/NONWOVEN LAMINATES", the disclosure of which has been incorporated by reference.

The absorbent core in the tested diapers was a dual layer absorbent having the general configuration set forth in FIGS. 5 and 6 except that there were no holes or apertures through either layer of the absorbent. The absorbent core included an upper layer and a lower layer with the upper layer extending from the front edge of the absorbent core to a location about two thirds of the total length of the absorbent core. The absorbent core included from about 10 to about 11 grams of wood pulp fibers and from about 10 to about 11 grams of superabsorbent material and, accordingly, included about 50 weight percent wood pulp fibers and about 50 weight percent superabsorbent material. The lower layer had a basis weight of about 230 grams per square meter and the upper layer had a basis weight of about 560 grams per square meter to provide a total basis weight of about 790 grams per square meter in the front section of the core and a basis weight of about 230 grams per square meter in the back section of the core. The absorbent core further defined a width in the crotch section of about 6.35 centimeters.

The surge layer was located between the absorbent core and the topsheet and was the same material as the surge layer in the Supreme diapers described in Comparative Example 2 except that it was modified to be coextensive with the absorbent core. The diapers also included a ventilation layer between the absorbent core and the backsheet of the diaper. The ventilation layer was made of the same material as the surge layer and was also coextensive with the absorbent core. The diapers also included an elasticized leg band assembly along about two thirds of the length of each longitudinal side edge of the diaper. The assembly had six (6) strands of elastomeric material laminated to a breathable, nonwoven fabric layer. The elastic strands were composed of LYCRA® elastomer aligned along the longitudinal length of the diaper to elasticize and gather the diaper legbands.

Four samples of the diapers were subjected to the Tracer Gas Test set forth above. The results are set forth in Table 1 below.

Example 2

Disposable diapers having the same general construction as the diapers described in connection with Example 1 were hand made and tested. The diapers were substantially the same as the Example 1 diapers except that the absorbent body was modified to include a plurality of holes therethrough in the region where the upper layer overlaid the lower layer as illustrated in FIGS. 5 and 6. The holes had a diameter of 1.27 centimeters to provide an open area of about 12 percent based on a total surface area of the absorbent body. Four samples of the diapers were subjected to the Tracer Gas Test set forth above. The results are set forth in Table 1 below.

Example 3

Disposable diapers having the same general construction as the diapers described in connection with Example 2 were hand made and tested. The diapers were substantially the same as the Example 2 diapers except that the ventilation layer between the absorbent body and the backsheet was removed. Four samples of the diapers were subjected to the Tracer Gas Test set forth above. The results are set forth in Table 1 below.

Example 4

Disposable diapers having the same general construction as the diapers described in connection with Example 2 were hand made and tested. The diapers were substantially the same as the Example 2 diapers except that the holes in the absorbent body had a diameter of 2.54 centimeters which also defined an open are of about 12 percent of the total surface are of the absorbent body. Four samples of the diapers were subjected to the Tracer Gas Test set forth above. The results are set forth in Table 1 below.

Example 5

Disposable diapers having the same general construction as the diapers described in connection with Example 2 were hand made and tested. The diapers were substantially the same as the Example 2 diapers except that the layered absorbent body was replaced with a non-layered absorbent body which included about 62 weight percent wood pulp fibers and about 38 weight percent superabsorbent and defined a basis weight in the front section of about 750 to about 850 grams per square meter and a basis weight in the back section of about 375 to about 425 grams per square meter. Four samples of the diapers were subjected to the Tracer Gas Test set forth above. The results are set forth in Table 1 below.

Example 6

Disposable diapers having the same general construction as the diapers described in connection with Example 2 were hand made and tested. The diapers were substantially the same as the Example 2 diapers except that the dual layered absorbent core was replaced with a laminate which included about 80 weight percent superabsorbent material commercially available from Stockhausen under the trade designation FAVOR SXM 880 overwrapped by a tissue layer of cellulosic fibers having a basis weight of about 26 grams per square meter. The absorbent body also included apertures therethrough having a diameter of 1.27 centimeters to provide an open area of about 12 percent of the total surface area of the absorbent body. Four samples of the diapers were subjected to the Tracer Gas Test set forth above. The results are set forth in Table 1 below.

Example 7

Disposable diapers having the same general construction as the diapers described in connection with Example 2 were hand made and tested. The diapers were substantially the same as the Example 2 diapers except that the absorbent body was replaced with a laminate which included about 80 weight percent superabsorbent material commercially available from Stockhausen under the trade designation FAVOR SXM 880 overwrapped by a tissue layer of cellulosic fibers having a basis weight of about 26 grams per square meter. The laminate was provided in four segments as representatively illustrated in FIGS. 3 and 4 which resulted in an open area for the absorbent body of about 40 percent of a total surface area of the absorbent body. Four samples of the diapers were subjected to the Tracer Gas Test set forth above. The results are set forth in Table 1 below.

Example 8

Disposable diapers having the same general construction as the diapers described in connection with Example 2 were hand made and tested. The diapers were substantially the same as the Example 2 diapers except that the backsheet was modified to define a water vapor transmission rate of about 1870 grams per square meter per 24 hours. Four samples of the diapers were subjected to the Tracer Gas Test set forth above. The results are set forth in Table 1 below.

Comparative Example 1

Disposable diapers having the same general construction as the Supreme Step 3 diapers as described in connection with Example 2 were hand made and tested. The diapers were substantially the same as the Example 2 diapers except that the backsheet was replaced with a 1 mil thick polyethylene film material having a water vapor transmission rate of less than 100 grams per square meter per hour. Four samples of the diapers were subjected to the Tracer Gas Test set forth above. The results are set forth in Table 1 below.

Comparative Example 2

Disposable diapers having the same general construction as those diapers commercially available from Kimberly-Clark Corporation under the trade designation HUGGIES® Supreme Step 3 were tested.

In essence, the Supreme diapers comprised an absorbent core consisting of a mixture of wood pulp fibers and superabsorbent material surrounded by a two piece cellulosic wrap sheet having a basis weight of about 16–21 grams per square meter. The absorbent core included from about 12.5 to about 13.5 grams of airlaid wood pulp fibers and from about 7.0 to about 8.5 grams of superabsorbent material. The superabsorbent material was purchased from Stockhausen under the trade designation FAVOR SXM 880. The superabsorbent material was homogeneously mixed with the pulp fibers to form a unitary layer having a density within the range of 0.25 to 0.35 grams per cubic centimeter. The homogeneous mixture of the superabsorbent material and the wood pulp fibers was zoned along the machine direction to provide a basis weight of from about 600 to about 700 grams per square meter in the front section of the absorbent core and a basis weight of from about 300 to about 350 grams per square meter in the back section of the absorbent core.

The Supreme diapers further included a composite backsheet comprising a vapor-permeable barrier layer adhesively laminated to a spunbond/meltblown/spunbond laminate material (hereinafter "SMS"). The SMS material had a basis weight of about 27 grams per square meter. The vapor-permeable barrier layer consisted of a polyolefin film which had a thickness of about 0.7 mil. and a basis weight of about 19.5 grams per square meter. The polyolefin film material was commercially available from Exxon Chemical Patents Incorporated, under the tradename EXXAIRE. The vapor-permeable barrier layer was adhered to the SMS laminate and positioned between the absorbent core and the SMS laminate material of the backsheet. The backsheet had a water vapor transmission rate of about 1500 grams per square meter per 24 hours. The absorbent core was sandwiched between the backsheet and a topsheet composed of a spunbond web of polypropylene fibers having a basis weight of about 17 grams per square meter. A surge management layer composed of a bonded carded web was located between the topsheet and the absorbent core. The surge layer included bicomponent fibers and defined an overall basis weight of about 83 grams per square meter. The surge layer was a homogeneous blend composed of about 60 weight percent polyethylene/polyester (PE/PET), sheath-core bicomponent fibers which had a fiber denier of about 3 d and about 40 weight percent single component polyester fibers which had a fiber denier of about 6 d and which have fiber lengths of from about 3.8 to about 5.08 centimeters. The surge layer further defined a width of about 10.2 centimeters and a length of about 16.5 centimeters. The front edge of the surge layer was located 5.1 centimeters from the front edge of the absorbent core.

The Supreme diapers further included a single component elasticized waistband and waist flap assembly at each longitudinal end of the diaper. The assembly had multiple strands of elastomeric material sandwiched and laminated between a polymer film layer and a nonwoven fabric layer. The polymer film was a 0.00075 inch thick film composed of a blend of a linear low density polyethylene and an ultra low density polyethylene. The nonwoven fabric layer was composed of a 20 grams per square meter web of polypropylene spunbond. The elastic strands were composed of about 8–16 strands of LYCRA® elastomer aligned along the cross-direction of the diaper to elasticize and gather the diaper waistbands and the internal waist flaps. The Supreme diapers also included length-wise containment flaps which extend the full length of the diaper and elasticized leg bands along each longitudinal side edge of the diaper. The elastic strands in the leg band and containment flaps were composed of LYCRA® elastomer aligned along the longitudinal length of the diaper to elasticize and gather the diaper legbands and the containment flaps.

Four samples of the diapers were subjected to the Tracer Gas Test set forth above. The results are set forth in Table 1 below.

TABLE 1

|  | Mean Dry Air Exc. Rate (cm³/min.) | Mean Wet Air Exc. Rate (cm³/min.) | Wet/Dry Ratio |
| --- | --- | --- | --- |
| Example 1 | 822 | 224 | 0.27 |
| Example 2 | 794 | 310 | 0.39 |
| Example 3 | 679 | 220 | 0.32 |
| Example 4 | 1050 | 360 | 0.34 |
| Example 5 | 758 | 190 | 0.25 |
| Example 6 | 724 | 240 | 0.33 |
| Example 7 | 677 | 153 | 0.23 |
| Example 8 | 495 | 316 | 0.63 |
| Comparative Ex. 1 | 51 | 110 | 2.16 |
| Comparative Ex. 2 | 513 | 171 | 0.33 |

The test results from Examples 1–8 and Comparative Examples 1 and 2 indicate that diapers made according to the present invention generally have improved levels of air exchange both when dry and when wet when compared to conventional diapers.

Example 9

Four samples of diapers having the same general construction as the diapers described in connection with Example 2 were hand made and tested according to the Skin Hydration Test set forth above. The diapers were substantially the same as the Example 2 diapers except that the diapers were similar in size to commercially available Step 4 size diapers, the absorbent body was a single layer having the same thickness throughout, and the apertures had a diameter of 2.54 centimeters. The diapers defined an average Skin Hydration Value of 8.1 grams per square meter per hour. The results are also set forth in Table 2 below.

Example 10

Four samples of diapers having the same general construction as the diapers described in connection with Example 6 were hand made and tested according to the Skin Hydration Test set forth above. The diapers were substantially the same as the Example 6 diapers except that the diapers were similar in size to commercially available Step 4 size diapers, the absorbent body defined a basis weight of about 560 grams per square meter and the apertures had a diameter of 2.54 centimeters. The diapers defined an average Skin Hydration Value of 2.8 grams per square meter per hour. The results are also set forth in Table 2 below.

Example 11

Four samples of diapers having the same general construction as the diapers described in connection with Example 7 were hand made and tested according to the Skin Hydration Test set forth above. The diapers were substantially the same as the Example 7 diapers except that the diapers were similar in size to commercially available Step 4 size diapers. The diapers defined an average Skin Hydration Value of 1.6 grams per square meter per hour. The results are also set forth in Table 2 below.

Comparative Example 3

Disposable diapers having the same general construction as those diapers commercially available from Kimberly-Clark Corporation under the trade designation HUGGIES® Supreme Step 4 were tested. In essence, the Step 4 sized Supreme diapers were similar to the Step 3 sized Supreme diapers described above in connection with Comparative Example 2 except that the size of the materials was greater.

Four samples of the diapers were subjected to the Skin Hydration Test set forth above. The diapers defined an average Skin Hydration Value of 19.3 grams per square meter per hour. The results are also set forth in Table 2 below.

TABLE 2

|  | Skin Hydration Value (g/m²/hr) |
| --- | --- |
| Example 9 | 8.1 |
| Example 10 | 2.8 |
| Example 11 | 1.6 |
| Comparative Ex. 3 | 19.3 |

The test results from Examples 9–11 and Comparative Example 3 indicate that diapers made according to the teachings of the present invention exhibit significantly improved Skin Hydration Values when compared to conventional diapers. Specifically, diapers made according to the present invention exhibited a 58 to 92 percent reduction in the Skin Hydration Value. While some reduction in the Skin Hydration Value was anticipated due to the increased amount of air exchange within the diapers, the magnitude of the reduction was unexpected.

Example 12

Samples of diapers having the same general construction as the diapers described in connection with Comparative Example 2 were hand made and tested. The diapers were substantially the same as the Comparative Example 2 diapers except that the backsheet was modified to define a water vapor transmission rate of about 3000 grams per square meter per 24 hours. The diapers were subjected to the *C. albicans* Viability Test set forth above. The samples of Example 12 and Comparative Example 4 (control) were tested on the volar forearms of each of seven test subjects. Approximately 0.01 milliliters of a 0.9 weight percent saline solution containing a suspension of 5.71 log of *C. albicans* colony forming units was delivered to the test site with micropipettes and the suspension was then spread uniformly across the test site. The sample diapers according to this example defined a mean *C. albicans* viability of 1.96 log of *C. albicans* colony forming units. Accordingly, compared to the mean *C. albicans* viability of the control (Comparative Example 4), the diapers according to this example defined a reduction in the *C. albicans* viability value of 26 percent.

Example 13

Samples of diapers having the same general construction as the diapers described in connection with Example 2 except that the backsheet defines a water vapor transmission rate of about 5000 grams per square meter per 24 hours are made. The diapers are subjected to the *C. albicans* Viability Test set forth above. The samples of Example 13 and Comparative Example 4 (control) are tested on the volar forearms of each of seven test subjects. Approximately 0.01 milliliters of a 0.9 weight percent saline solution containing a suspension of 5.71 log of *C. albicans* colony forming units is delivered to the test site with micropipettes and the suspension is then spread uniformly across the test site. It is anticipated that the sample diapers according to this example would define a mean *C. albicans* viability of more likely less than 1.75 and likely less than 1.50 log of *C. albicans* colony forming units. Accordingly, compared to the mean *C. albicans* viability of the control (Comparative Example 4), it is anticipated that the diapers according to this example will define a reduction in the *C. albicans* viability value of more likely about 34 percent and likely about 43 percent.

Comparative Example 4

Samples of diapers having the same general construction as the diapers described in connection with Comparative Example 2 were hand made and tested. The diapers were substantially the same as the Comparative Example 2 diapers except the backsheet was replaced with a 1.0 mil thick polyethylene film material having a water vapor transmission rate of less than 100 grams per square meter per 24 hours. The diapers were subjected to the *C. albicans* Viability Test set forth above on the volar forearms of each of seven test subjects. Approximately 0.01 milliliters of a 0.9 weight percent saline solution containing a suspension of 5.71 log of *C. albicans* colony forming units was delivered to the test site with micropipettes and the suspension was then spread uniformly across the test site. The sample diapers according to this example defined a mean *C. albicans* viability of 2.65 log of *C. albicans* colony forming units.

Example 14

Samples of diapers having the same general construction as the diapers described in connection with Example 13 were machine made and tested. In particular, the backsheet of the diapers defined a water vapor transmission rate of about 5000 grams per square meter per 24 hours. The diapers were subjected to the *C. albicans* Viability Test set forth above. The samples of Example 14 and Comparative Example 5 (control) were tested on the volar forearms of each of twenty test subjects. Approximately 0.01 milliliters of a 0.9 weight percent saline solution containing a suspension of 4.92 log of *C. albicans* colony forming units was delivered to the test site with micropipettes and the suspension was then spread uniformly across the test site. The sample diapers according to this example defined a mean *C. albicans* viability of 1.26 log of *C. albicans* colony forming units. Accordingly, compared to the mean *C. albicans* viability of the control (Comparative Example 5), the diapers according to this example defined a reduction in the *C. albicans* viability value of 61 percent.

Comparative Example 5

Samples of diapers having the same general construction as the diapers described in connection with Comparative Example 4 were machine made and tested. In particular, the backsheet of the diapers included a 1.0 mil thick polyethylene film material having a water vapor transmission rate of less than 100 grams per square meter per 24 hours. The diapers were subjected to the *C. albicans* Viability Test set forth above on the volar forearms of each of twenty test subjects. Approximately 0.01 milliliters of a 0.9 weight percent saline solution containing a suspension of 4.92 log of *C. albicans* colony forming units was delivered to the test site with micropipettes and the suspension was then spread uniformly across the test site. The sample diapers according to this example defined a mean *C. albicans* viability of 3.26 log of *C. albicans* colony forming units.

The test results from Examples 12 and 14 and the expected results from Example 13 show that diapers made according to the present invention exhibit a reduced viability and incidence of microbial infection when compared to conventional absorbent diapers and the test results from Comparative Examples 4 and 5. It is clear that such reduced microbial viability is achieved by reducing the occlusion of the skin by increasing the breathability of the diaper both when dry and when wet.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. A disposable absorbent article comprising an absorbent, a front waist section, a rear waist section and an intermediate section which interconnects said front and rear waist sections wherein said absorbent article defines a *C. albicans* viability which is less than about 85 percent of the *C. albicans* viability of a control calculated according to a *C. albicans* Viability Test as set forth herein.

2. The absorbent article of claim 1 wherein said *C. albicans* viability is less than about 80 percent of the *C. albicans* viability of the control calculated according to said *C. albicans* Viability Test.

3. The absorbent article of claim 1 wherein said *C. albicans* viability is less than about 60 percent of the *C. albicans* viability of the control calculated according to said *C. albicans* Viability Test.

4. The absorbent article of claim 1 wherein said absorbent article further defines a Wet Air Exchange Rate of at least about 190 cubic centimeters per minute calculated according to a Tracer Gas Test as set forth herein.

5. The absorbent article of claim 1 wherein said absorbent article defines a Dry Air Exchange Rate of at least about 525 cubic centimeters per minute calculated according to a Tracer Gas Test as set forth herein.

6. The absorbent article of claim 1 wherein said absorbent article defines a Skin Hydration Value of less than about 18 grams per square meter per hour calculated according to a Skin Hydration Test set forth herein.

7. A disposable absorbent article which comprises:
   a) a vapor permeable backsheet which defines a Water Vapor Transmission Rate of at least about 1000 grams per square meter per 24 hours calculated according to a Water Vapor Transmission Test as set forth herein;
   b) a liquid permeable topsheet which is positioned in facing relation with said backsheet; and
   c) an absorbent body located between said backsheet and said topsheet wherein said absorbent article defines a *C. albicans* viability which is less than about 85 percent of the *C. albicans* viability of a control calculated according to a *C. albicans* Viability Test as set forth herein.

8. The absorbent article of claim 7 wherein said *C. albicans* viability is less than about 80 percent of the *C. albicans* viability of the control calculated according to said *C. albicans* Viability Test.

9. The absorbent article of claim 7 wherein said *C. albicans* viability is less than about 60 percent of the *C. albicans* viability of the control calculated according to said *C. albicans* Viability Test.

10. The absorbent article of claim 7 wherein said absorbent article further defines a Wet Air Exchange Rate of at least about 190 cubic centimeters per minute calculated according to a Tracer Gas Test as set forth herein.

11. The absorbent article of claim 7 wherein said absorbent article defines a Dry Air Exchange Rate of at least about 525 cubic centimeters per minute calculated according to a Tracer Gas Test as set forth herein.

12. The absorbent article of claim 7 wherein said absorbent article defines a Skin Hydration Value of less than about 18 grams per square meter per hour calculated according to a Skin Hydration Test set forth herein.

13. The absorbent article of claim 7 wherein said vapor permeable backsheet is substantially liquid impermeable.

14. The absorbent article of claim 7 wherein said vapor permeable backsheet defines a Hydrohead Value of at least about 60 centimeters calculated according to a Hydrostatic Pressure Test as set forth herein.

15. The absorbent article of claim 7 wherein said Water Vapor Transmission Rate of said vapor permeable backsheet is at least about 1500 grams per square meter per 24 hours calculated according to said Water Vapor Transmission Test.

16. A disposable absorbent article which defines a front waist section, a rear waist section, and an intermediate section which interconnects said front and rear waist sections, said absorbent article comprising:
   a) a vapor permeable backsheet which defines a Water Vapor Transmission Rate of at least about 1000 grams per square meter per 24 hours calculated according to a Water Vapor Transmission Test as set forth herein;
   b) a liquid permeable topsheet which is positioned in facing relation with said backsheet;
   c) an absorbent body located between said backsheet and said topsheet which defines zones of high air permeability for improved air exchange; and
   d) a ventilation layer located between said backsheet and said absorbent body wherein said absorbent article defines a *C. albicans* viability which is less than about 85 percent of the *C. albicans* viability of a control calculated according to a *C. albicans* Viability Test as set forth herein.

17. The absorbent article of claim 16 wherein said vapor permeable backsheet is substantially liquid impermeable.

18. The absorbent article of claim 16 wherein said Water Vapor Transmission Rate of said vapor permeable backsheet is at least about 1500 grams per square meter per 24 hours calculated according to said Water Vapor Transmission Test.

19. The absorbent article of claim 16 wherein said zones of high air permeability in said absorbent body define a Frazier Porosity which is at least about 10 percent greater than a Frazier Porosity of portions of said absorbent body adjacent to said air passageways.

20. The absorbent article of claim 16 wherein said zones of high air permeability comprise from about 5 to about 75 percent of a total surface area of said absorbent body.

21. The absorbent article of claim 16 wherein said *C. albicans* viability is less than about 80 percent of the *C. albicans* viability of the control calculated according to said *C. albicans* Viability Test.

22. The absorbent article of claim 16 wherein said absorbent article further defines a Wet Air Exchange Rate of at least about 190 cubic centimeters per minute calculated according to a Tracer Gas Test as set forth herein.

23. The absorbent article of claim 16 wherein said absorbent article defines a Skin Hydration Value of less than about 18 grams per square meter per hour calculated according to a Skin Hydration Test set forth herein.

24. The absorbent article of claim 16 wherein said ventilation layer comprises a hydrophobic, nonwoven material having a thickness of at least about 0.10 centimeters and a basis weight of from about 20 to about 120 grams per square meter.

25. The absorbent article of claim 16 and further comprising a surge management layer which is located between said topsheet and said absorbent wherein said surge management layer comprises a nonwoven material having a basis weight of from about 30 to about 120 grams per square meter.

* * * * *